United States Patent
Wolf et al.

(10) Patent No.: US 12,178,666 B2
(45) Date of Patent: Dec. 31, 2024

(54) FIDUCIAL MARKER

(71) Applicant: Augmedics Ltd., Yokneam Illit (IL)

(72) Inventors: Stuart Wolf, Yokneam (IL); Nissan Elimelech, Beerotaim (IL)

(73) Assignee: Augmedics Ltd., Yokneam Illit (IL)

( * ) Notice: Subject to any disclaimer, the term of this patent is extended or adjusted under 35 U.S.C. 154(b) by 352 days.

(21) Appl. No.: 17/585,629

(22) Filed: Jan. 27, 2022

(65) Prior Publication Data

US 2022/0142730 A1 May 12, 2022

Related U.S. Application Data

(63) Continuation-in-part of application No. PCT/IB2020/056893, filed on Jul. 22, 2020, which is a continuation-in-part of application No. 16/524,258, filed on Jul. 29, 2019, now Pat. No. 11,980,506.

(51) Int. Cl.
*A61B 90/00* (2016.01)
*A61B 90/57* (2016.01)
*G02B 27/01* (2006.01)

(52) U.S. Cl.
CPC ............ *A61B 90/39* (2016.02); *A61B 90/361* (2016.02); *A61B 90/57* (2016.02); *G02B 27/017* (2013.01); *A61B 2090/365* (2016.02); *A61B 2090/3966* (2016.02); *A61B 2090/3983* (2016.02)

(58) Field of Classification Search
CPC ....... A61B 90/39; A61B 90/361; A61B 90/57; A61B 2090/365; A61B 2090/3966; A61B 2090/3983; G02B 27/017
See application file for complete search history.

(56) References Cited

U.S. PATENT DOCUMENTS

| | | |
|---|---|---|
| 3,101,715 A | 8/1963 | Glassman |
| 3,690,776 A | 9/1972 | Zaporoshan |
| 4,459,358 A | 7/1984 | Berke |
| 4,711,512 A | 12/1987 | Upatnieks |
| 4,863,238 A | 9/1989 | Brewster |
| 4,944,739 A | 7/1990 | Torre |
| 5,100,420 A | 3/1992 | Green et al. |
| 5,147,365 A | 9/1992 | Whitlock et al. |

(Continued)

FOREIGN PATENT DOCUMENTS

| | | |
|---|---|---|
| CA | 3022448 A1 | 2/2018 |
| CA | 3034314 A1 | 2/2018 |

(Continued)

OTHER PUBLICATIONS

US 11,395,705 B2, 09/2022, Lang (withdrawn)

(Continued)

*Primary Examiner* — Carl H Layno
*Assistant Examiner* — Aya Ziad Bakkar
(74) *Attorney, Agent, or Firm* — KNOBBE, MARTENS, OLSON & BEAR, LLP

(57) ABSTRACT

A medical marking device, consisting of a radiotransparent plate having a first plurality of radiopaque elements embedded therein in a first predefined pattern and a second plurality of optical reflectors positioned on a surface in proximity to the plate in a second predefined pattern. The device also includes a sigmoid mounting arm having a first end connected to the radiotransparent plate and a second end containing one or more fastening receptacles.

14 Claims, 8 Drawing Sheets

(56) References Cited

U.S. PATENT DOCUMENTS

| | | |
|---|---|---|
| 5,357,292 A | 10/1994 | Wiedner |
| 5,410,802 A | 5/1995 | Buckley |
| 5,441,042 A | 8/1995 | Putman |
| 5,442,146 A | 8/1995 | Bell |
| 5,510,832 A | 4/1996 | Garcia |
| D370,309 S | 5/1996 | Stucky |
| 5,620,188 A | 4/1997 | McCurry et al. |
| 5,636,255 A | 6/1997 | Ellis |
| 5,665,092 A | 9/1997 | Mangiardi et al. |
| 5,743,731 A | 4/1998 | Lares et al. |
| 5,771,121 A | 6/1998 | Hentschke |
| 5,792,046 A | 8/1998 | Dobrovolny |
| 5,841,507 A | 11/1998 | Barnes et al. |
| 6,006,126 A | 12/1999 | Cosman |
| 6,038,467 A | 3/2000 | De Bliek et al. |
| 6,125,164 A | 9/2000 | Murphy |
| 6,138,530 A | 10/2000 | McClure |
| 6,147,805 A | 11/2000 | Fergason |
| 6,227,667 B1 | 5/2001 | Halldorsson |
| 6,256,529 B1 | 7/2001 | Holupka et al. |
| 6,285,505 B1 | 9/2001 | Melville et al. |
| 6,314,310 B1 | 11/2001 | Ben-Haim et al. |
| 6,349,001 B1 | 2/2002 | Spitzer |
| 6,444,192 B1 | 9/2002 | Mattrey |
| 6,449,090 B1 | 9/2002 | Omar |
| 6,456,405 B2 | 9/2002 | Horikoshi et al. |
| 6,456,868 B2 | 9/2002 | Saito et al. |
| 6,474,159 B1 | 11/2002 | Foxlin et al. |
| 6,518,939 B1 | 2/2003 | Kikuchi |
| 6,527,777 B2 | 3/2003 | Justin |
| 6,529,331 B2 | 3/2003 | Massof et al. |
| 6,549,645 B1 | 4/2003 | Oikawa |
| 6,578,962 B1 | 6/2003 | Amir et al. |
| 6,609,022 B2 | 8/2003 | Vilsmeier et al. |
| 6,610,009 B2 | 8/2003 | Person |
| D480,476 S | 10/2003 | Martinson et al. |
| 6,659,611 B2 | 12/2003 | Amir et al. |
| 6,675,040 B1 | 1/2004 | CoSman |
| 6,683,584 B2 | 1/2004 | Ronzani et al. |
| 6,690,964 B2 | 2/2004 | Bieger et al. |
| 6,714,810 B2 | 3/2004 | Grzeszczuk et al. |
| 6,737,425 B1 | 5/2004 | Yamamoto |
| 6,740,882 B2 | 5/2004 | Weinberg |
| 6,757,068 B2 | 6/2004 | Foxlin |
| 6,759,200 B1 | 7/2004 | Stanton |
| 6,847,336 B1 | 1/2005 | Lemelson et al. |
| 6,856,324 B2 | 2/2005 | Sauer |
| 6,856,826 B2 | 2/2005 | Seeley et al. |
| 6,891,518 B2 | 5/2005 | Sauer et al. |
| 6,900,777 B1 | 5/2005 | Hebert et al. |
| 6,919,867 B2 | 7/2005 | Sauer |
| 6,921,167 B2 | 7/2005 | Nagata |
| 6,966,668 B2 | 11/2005 | Cugini |
| 6,980,849 B2 | 12/2005 | Sasso |
| 6,993,374 B2 | 1/2006 | Sasso |
| 6,997,552 B1 | 2/2006 | Hung |
| 6,999,239 B1 | 2/2006 | Martins et al. |
| 7,000,262 B2 | 2/2006 | Bielefeld |
| 7,035,371 B2 | 4/2006 | Boese et al. |
| 7,043,961 B2 | 5/2006 | Pandey et al. |
| 7,072,435 B2 | 7/2006 | Metz et al. |
| 7,103,233 B2 | 9/2006 | Stearns |
| 7,107,091 B2 | 9/2006 | Jutras et al. |
| 7,112,656 B2 | 9/2006 | Desnoyers |
| 7,141,812 B2 | 11/2006 | Appleby |
| 7,157,459 B2 | 1/2007 | Ohta |
| 7,169,785 B2 | 1/2007 | Timmer |
| 7,171,255 B2 | 1/2007 | Holupka et al. |
| 7,176,936 B2 | 2/2007 | Sauer et al. |
| 7,187,792 B2 | 3/2007 | Fu |
| 7,190,331 B2 | 3/2007 | Genc et al. |
| 7,194,295 B2 | 3/2007 | Vilsmeier |
| 7,215,322 B2 | 5/2007 | Genc et al. |
| 7,229,078 B2 | 6/2007 | Lechot |
| 7,231,076 B2 | 6/2007 | Fu |
| 7,235,076 B2 | 6/2007 | Pacheco |
| 7,239,330 B2 | 7/2007 | Sauer et al. |
| 7,241,292 B2 | 7/2007 | Hooven |
| 7,259,266 B2 | 8/2007 | Carter |
| 7,260,426 B2 | 8/2007 | Schweikard |
| 7,269,192 B2 | 9/2007 | Hayashi |
| 7,281,826 B2 | 10/2007 | Huang |
| 7,315,636 B2 | 1/2008 | Kuduvalli |
| 7,320,556 B2 | 1/2008 | Vagn-Erik |
| 7,330,578 B2 | 2/2008 | Wang |
| 7,359,535 B2 | 4/2008 | Salla |
| 7,364,314 B2 | 4/2008 | Nilsen et al. |
| 7,366,934 B1 | 4/2008 | Narayan et al. |
| 7,379,077 B2 | 5/2008 | Bani-Hashemi |
| 7,431,453 B2 | 10/2008 | Hogan |
| 7,435,219 B2 | 10/2008 | Kim |
| 7,450,743 B2 | 11/2008 | Sundar et al. |
| 7,458,977 B2 | 12/2008 | McGinley |
| 7,462,852 B2 | 12/2008 | Appleby |
| 7,493,153 B2 | 2/2009 | Ahmed et al. |
| 7,505,617 B2 | 3/2009 | Fu |
| 7,507,968 B2 | 3/2009 | Wollenweber |
| 7,518,136 B2 | 4/2009 | Appleby |
| 7,525,735 B2 | 4/2009 | Sottilare et al. |
| D592,691 S | 5/2009 | Chang |
| D592,692 S | 5/2009 | Chang |
| D592,693 S | 5/2009 | Chang |
| 7,536,216 B2 | 5/2009 | Geiger et al. |
| 7,542,791 B2 | 6/2009 | Mire |
| 7,556,428 B2 | 7/2009 | Sukovic et al. |
| 7,557,824 B2 | 7/2009 | Holliman |
| 7,563,228 B2 | 7/2009 | Ma et al. |
| 7,567,834 B2 | 7/2009 | Clayton |
| 7,570,791 B2 | 8/2009 | Frank et al. |
| 7,586,686 B1 | 9/2009 | Hall |
| D602,620 S | 10/2009 | Cristoforo |
| 7,605,826 B2 | 10/2009 | Sauer |
| 7,606,613 B2 | 10/2009 | Simon et al. |
| 7,607,775 B2 | 10/2009 | Hermanson |
| 7,620,223 B2 | 11/2009 | Xu |
| 7,623,902 B2 | 11/2009 | Pacheco |
| 7,627,085 B2 | 12/2009 | Boyden et al. |
| 7,630,753 B2 | 12/2009 | Simon et al. |
| 7,633,501 B2 | 12/2009 | Wood |
| 7,645,050 B2 | 1/2010 | Wilt |
| 7,653,226 B2 | 1/2010 | Guhring et al. |
| 7,657,075 B2 | 2/2010 | Viswanathan |
| 7,689,019 B2 | 3/2010 | Boese |
| 7,689,042 B2 | 3/2010 | Brunner |
| 7,689,320 B2 | 3/2010 | Prisco |
| 7,699,486 B1 | 4/2010 | Beiner |
| 7,699,793 B2 | 4/2010 | Gotte |
| 7,719,769 B2 | 5/2010 | Sugihara et al. |
| D617,825 S | 6/2010 | Chang |
| 7,734,327 B2 | 6/2010 | Colquhoun |
| D619,285 S | 7/2010 | Cristoforo |
| 7,751,865 B2 | 7/2010 | Jascob et al. |
| 7,758,204 B2 | 7/2010 | Klipstein |
| 7,768,702 B2 | 8/2010 | Hirose et al. |
| 7,769,236 B2 | 8/2010 | Fiala |
| 7,773,074 B2 | 8/2010 | Arenson et al. |
| 7,774,044 B2 | 8/2010 | Sauer et al. |
| 7,822,483 B2 | 10/2010 | Stone et al. |
| D628,307 S | 11/2010 | Krause-Bonte |
| 7,826,902 B2 | 11/2010 | Stone et al. |
| 7,831,073 B2 | 11/2010 | Fu et al. |
| 7,831,096 B2 | 11/2010 | Williamson |
| 7,835,778 B2 | 11/2010 | Foley |
| 7,835,784 B2 | 11/2010 | Mire |
| 7,837,987 B2 | 11/2010 | Shi |
| 7,840,093 B2 | 11/2010 | Fu et al. |
| 7,840,253 B2 | 11/2010 | Tremblay et al. |
| 7,840,256 B2 | 11/2010 | Lakin et al. |
| 7,853,305 B2 | 12/2010 | Simon |
| 7,854,705 B2 | 12/2010 | Pawluczyk |
| 7,857,271 B2 | 12/2010 | Lees |
| 7,860,282 B2 | 12/2010 | Boese |
| D630,766 S | 1/2011 | Harbin |
| 7,865,269 B2 | 1/2011 | Prisco |

(56) References Cited

U.S. PATENT DOCUMENTS

| | | |
|---|---|---|
| 7,874,686 B2 | 1/2011 | Rossner et al. |
| 7,881,770 B2 | 2/2011 | Melkent et al. |
| 7,893,413 B1 | 2/2011 | Appleby |
| 7,894,649 B2 | 2/2011 | Fu |
| 7,920,162 B2 | 4/2011 | Masini et al. |
| 7,922,391 B2 | 4/2011 | Essenreiter et al. |
| 7,938,553 B1 | 5/2011 | Beiner |
| 7,945,310 B2 | 5/2011 | Gattani |
| 7,953,471 B2 | 5/2011 | Clayton |
| 7,969,383 B2 | 6/2011 | Eberl et al. |
| 7,974,677 B2 | 7/2011 | Mire |
| 7,985,756 B2 | 7/2011 | Barlow |
| 7,991,557 B2 | 8/2011 | Liew |
| 7,993,353 B2 | 8/2011 | Robner et al. |
| 7,996,064 B2 | 8/2011 | Simon et al. |
| 8,004,524 B2 | 8/2011 | Deinzer |
| 8,021,300 B2 | 9/2011 | Ma et al. |
| 8,022,984 B2 | 9/2011 | Cheong |
| 8,045,266 B2 | 10/2011 | Nakamura |
| 8,060,181 B2 | 11/2011 | Ponce |
| 8,068,581 B2 | 11/2011 | Boese et al. |
| 8,068,896 B2 | 11/2011 | Daghighian |
| 8,077,943 B2 | 12/2011 | Wiliams |
| 8,079,957 B2 | 12/2011 | Ma et al. |
| 8,081,812 B2 | 12/2011 | Kreiser |
| 8,085,075 B2 | 12/2011 | Huffman |
| 8,085,897 B2 | 12/2011 | Morton |
| 8,090,175 B2 | 1/2012 | Fu |
| 8,092,400 B2 | 1/2012 | Warkentine |
| 8,108,072 B2 | 1/2012 | Zhao |
| 8,112,292 B2 | 2/2012 | Simon |
| 8,116,847 B2 | 2/2012 | Gattani et al. |
| 8,120,847 B2 | 2/2012 | Chang |
| 8,121,255 B2 | 2/2012 | Sugiyama |
| 8,155,479 B2 | 4/2012 | Hoffman |
| 8,180,132 B2 | 5/2012 | Gorges et al. |
| 8,180,429 B2 | 5/2012 | Sasso |
| 8,208,599 B2 | 6/2012 | Ye |
| 8,216,211 B2 | 7/2012 | Mathis et al. |
| 8,221,402 B2 | 7/2012 | Francischelli |
| 8,239,001 B2 | 8/2012 | Verard et al. |
| 8,244,012 B2 | 8/2012 | Liang et al. |
| 8,253,778 B2 | 8/2012 | Atsushi |
| 8,271,069 B2 | 9/2012 | Jascob et al. |
| 8,280,491 B2 | 10/2012 | Kuduvalli et al. |
| 8,285,021 B2 | 10/2012 | Boese |
| 8,300,315 B2 | 10/2012 | Kobayashi |
| 8,305,685 B2 | 11/2012 | Heine |
| 8,306,305 B2 | 11/2012 | Porat et al. |
| 8,309,932 B2 | 11/2012 | Haselman |
| 8,317,320 B2 | 11/2012 | Huang |
| 8,328,815 B2 | 12/2012 | Farr et al. |
| 8,335,553 B2 | 12/2012 | Rubner |
| 8,335,557 B2 | 12/2012 | Maschke |
| 8,340,379 B2 | 12/2012 | Razzaque et al. |
| 8,369,925 B2 | 2/2013 | Giesel |
| 8,386,022 B2 | 2/2013 | Jutras et al. |
| 8,394,144 B2 | 3/2013 | Zehavi |
| 8,398,541 B2 | 3/2013 | Dimaio et al. |
| 8,444,266 B2 | 5/2013 | Waters |
| 8,457,719 B2 | 6/2013 | Moctezuma De La Barrera et al. |
| 8,467,851 B2 | 6/2013 | Mire et al. |
| 8,469,902 B2 | 6/2013 | Dick |
| 8,475,470 B2 | 7/2013 | Von Jako |
| 8,494,612 B2 | 7/2013 | Vetter et al. |
| 8,509,503 B2 | 8/2013 | Nahum et al. |
| 8,511,827 B2 | 8/2013 | Hua et al. |
| 8,531,394 B2 | 9/2013 | Maltz |
| 8,540,364 B2 | 9/2013 | Waters |
| 8,545,012 B2 | 10/2013 | Waters |
| 8,548,567 B2 | 10/2013 | Maschke et al. |
| 8,556,883 B2 | 10/2013 | Saleh |
| 8,559,596 B2 | 10/2013 | Thomson |
| 8,567,945 B2 | 10/2013 | Waters |
| 8,571,353 B2 | 10/2013 | Watanabe |
| 8,585,598 B2 | 11/2013 | Razzaque et al. |
| 8,600,001 B2 | 12/2013 | Schweizer |
| 8,600,477 B2 | 12/2013 | Beyar |
| 8,605,199 B2 | 12/2013 | Imai |
| 8,611,988 B2 | 12/2013 | Miyamoto |
| 8,612,024 B2 | 12/2013 | Stone et al. |
| 8,634,897 B2 | 1/2014 | Simon |
| 8,641,621 B2 | 2/2014 | Razzaque et al. |
| 8,643,950 B2 | 2/2014 | König |
| 8,644,907 B2 | 2/2014 | Hartmann et al. |
| 8,674,902 B2 | 3/2014 | Park |
| 8,686,923 B2 | 4/2014 | Eberl et al. |
| 8,690,581 B2 | 4/2014 | Ruf et al. |
| 8,690,776 B2 | 4/2014 | Razzaque et al. |
| 8,692,845 B2 | 4/2014 | Fedorovskaya et al. |
| 8,693,632 B2 | 4/2014 | Allison |
| 8,694,075 B2 | 4/2014 | Groszmann |
| 8,699,765 B2 | 4/2014 | Hao |
| 8,705,829 B2 | 4/2014 | Frank |
| 8,737,708 B2 | 5/2014 | Hartmann et al. |
| 8,746,887 B2 | 6/2014 | Shestak |
| 8,764,025 B1 | 7/2014 | Gao |
| 8,784,450 B2 | 7/2014 | Moskowitz et al. |
| 8,786,689 B1 | 7/2014 | Liu |
| D710,545 S | 8/2014 | Wu |
| D710,546 S | 8/2014 | Wu |
| 8,827,934 B2 | 9/2014 | Chopra et al. |
| 8,831,706 B2 | 9/2014 | Fu |
| 8,836,768 B1 | 9/2014 | Rafii et al. |
| 8,838,199 B2 | 9/2014 | Simon et al. |
| 8,848,977 B2 | 9/2014 | Bammer et al. |
| 8,855,395 B2 | 10/2014 | Baturin |
| 8,878,900 B2 | 11/2014 | Yang et al. |
| 8,879,815 B2 | 11/2014 | Miao et al. |
| 8,885,177 B2 | 11/2014 | Ben-Yishai et al. |
| 8,890,772 B2 | 11/2014 | Woo |
| 8,890,773 B1 | 11/2014 | Pederson |
| 8,890,943 B2 | 11/2014 | Lee |
| 8,897,514 B2 | 11/2014 | Feikas |
| 8,900,131 B2 | 12/2014 | Chopra et al. |
| 8,903,150 B2 | 12/2014 | Star-Lack |
| 8,908,952 B2 | 12/2014 | Isaacs et al. |
| 8,911,358 B2 | 12/2014 | Koninckx et al. |
| 8,917,268 B2 | 12/2014 | Johnsen |
| 8,920,776 B2 | 12/2014 | Gaiger |
| 8,922,589 B2 | 12/2014 | Laor |
| 8,941,559 B2 | 1/2015 | Bar-Zeev et al. |
| 8,942,455 B2 | 1/2015 | Chou |
| 8,950,877 B2 | 2/2015 | Northey et al. |
| 8,953,246 B2 | 2/2015 | Koenig |
| 8,965,583 B2 | 2/2015 | Ortmaier et al. |
| 8,969,829 B2 | 3/2015 | Wollenweber |
| 8,989,349 B2 | 3/2015 | Thomson |
| 8,992,580 B2 | 3/2015 | Bar |
| 8,994,729 B2 | 3/2015 | Nakamura |
| 8,994,795 B2 | 3/2015 | Oh |
| 9,004,711 B2 | 4/2015 | Gerolemou |
| 9,005,211 B2 | 4/2015 | Brundobler et al. |
| 9,011,441 B2 | 4/2015 | Bertagnoli et al. |
| 9,057,759 B2 | 6/2015 | Klingenbeck |
| 9,060,757 B2 | 6/2015 | Lawson et al. |
| 9,066,751 B2 | 6/2015 | Sasso |
| 9,081,436 B1 | 7/2015 | Berme |
| 9,084,635 B2 | 7/2015 | Nuckley et al. |
| 9,085,643 B2 | 7/2015 | Svanborg |
| 9,087,471 B2 | 7/2015 | Miao |
| 9,100,643 B2 | 8/2015 | McDowall |
| 9,101,394 B2 | 8/2015 | Arata et al. |
| 9,104,902 B2 | 8/2015 | Xu et al. |
| 9,111,175 B2 | 8/2015 | Strommer |
| 9,123,155 B2 | 9/2015 | Cunningham et al. |
| 9,125,556 B2 | 9/2015 | Zehavi |
| 9,129,054 B2 | 9/2015 | Nawana et al. |
| 9,129,372 B2 | 9/2015 | Kriston |
| 9,132,361 B2 | 9/2015 | Smithwick |
| 9,135,706 B2 | 9/2015 | Zagorchev et al. |
| 9,141,873 B2 | 9/2015 | Takemoto |
| 9,142,020 B2 | 9/2015 | Deguise et al. |
| 9,149,317 B2 | 10/2015 | Arthur et al. |

(56) References Cited

U.S. PATENT DOCUMENTS

| | | |
|---|---|---|
| 9,165,203 B2 | 10/2015 | McCarthy |
| 9,165,362 B2 | 10/2015 | Siewerdsen et al. |
| 9,179,984 B2 | 11/2015 | Teichman et al. |
| D746,354 S | 12/2015 | Chang |
| 9,208,916 B2 | 12/2015 | Appleby |
| 9,220,573 B2 | 12/2015 | Kendrick et al. |
| 9,225,895 B2 | 12/2015 | Kozinski |
| 9,232,982 B2 | 1/2016 | Soler et al. |
| 9,235,934 B2 | 1/2016 | Mandella |
| 9,240,046 B2 | 1/2016 | Carrell et al. |
| 9,244,278 B2 | 1/2016 | Sugiyama et al. |
| 9,247,240 B2 | 1/2016 | Park |
| 9,259,192 B2 | 2/2016 | Ishihara |
| 9,265,572 B2 | 2/2016 | Fuchs et al. |
| 9,269,192 B2 | 2/2016 | Kobayashi |
| 9,283,052 B2 | 3/2016 | Ponce |
| 9,286,730 B2 | 3/2016 | Bar-Zeev et al. |
| 9,289,267 B2 | 3/2016 | Sauer et al. |
| 9,294,222 B2 | 3/2016 | Proctor, Jr. |
| 9,300,949 B2 | 3/2016 | Ahearn |
| 9,305,354 B2 | 4/2016 | Burlon et al. |
| 9,310,591 B2 | 4/2016 | Hua et al. |
| 9,320,474 B2 | 4/2016 | Demri |
| 9,323,055 B2 | 4/2016 | Baillot |
| 9,330,477 B2 | 5/2016 | Rappel |
| 9,335,547 B2 | 5/2016 | Takano et al. |
| 9,335,567 B2 | 5/2016 | Nakamura |
| 9,341,704 B2 | 5/2016 | Picard |
| 9,344,686 B2 | 5/2016 | Moharir |
| 9,349,066 B2 | 5/2016 | Koo |
| 9,349,520 B2 | 5/2016 | Demetriou |
| 9,364,294 B2 | 6/2016 | Razzaque et al. |
| 9,370,332 B2 | 6/2016 | Paladini et al. |
| 9,373,166 B2 | 6/2016 | Azar |
| 9,375,639 B2 | 6/2016 | Kobayashi et al. |
| 9,378,558 B2 | 6/2016 | Kajiwara et al. |
| 9,380,287 B2 | 6/2016 | Nistico |
| 9,387,008 B2 | 7/2016 | Sarvestani |
| 9,392,129 B2 | 7/2016 | Simmons |
| 9,395,542 B2 | 7/2016 | Tilleman et al. |
| 9,398,936 B2 | 7/2016 | Razzaque et al. |
| 9,400,384 B2 | 7/2016 | Griffith |
| 9,414,041 B2 | 8/2016 | Ko |
| 9,424,611 B2 | 8/2016 | Kanjirathinkal et al. |
| 9,424,641 B2 | 8/2016 | Wiemker |
| 9,427,286 B2 | 8/2016 | Siewerdsen et al. |
| 9,438,894 B2 | 9/2016 | Park |
| 9,443,488 B2 | 9/2016 | Borenstein |
| 9,453,804 B2 | 9/2016 | Tahtali |
| 9,456,878 B2 | 10/2016 | Macfarlane et al. |
| 9,465,235 B2 | 10/2016 | Chang |
| 9,468,373 B2 | 10/2016 | Larsen |
| 9,470,908 B1 | 10/2016 | Frankel |
| 9,473,766 B2 | 10/2016 | Douglas |
| 9,492,222 B2 | 11/2016 | Singh |
| 9,495,585 B2 | 11/2016 | Bicer et al. |
| 9,498,132 B2 | 11/2016 | Pugh et al. |
| 9,498,231 B2 | 11/2016 | Haider et al. |
| 9,499,999 B2 | 11/2016 | Zhou |
| 9,507,155 B2 | 11/2016 | Morimoto |
| 9,513,495 B2 | 12/2016 | Waters |
| 9,521,966 B2 | 12/2016 | Schwartz |
| 9,526,443 B1 | 12/2016 | Berme |
| 9,530,382 B2 | 12/2016 | Simmons |
| 9,532,846 B2 | 1/2017 | Nakamura |
| 9,532,849 B2 | 1/2017 | Anderson et al. |
| 9,533,407 B1 | 1/2017 | Ragner |
| 9,538,962 B1 | 1/2017 | Hannaford et al. |
| 9,545,233 B2 | 1/2017 | Sirpad |
| 9,546,779 B2 | 1/2017 | Rementer |
| 9,547,174 B2 | 1/2017 | Gao et al. |
| 9,547,940 B1 | 1/2017 | Sun et al. |
| 9,557,566 B2 | 1/2017 | Fujimaki |
| 9,560,318 B2 | 1/2017 | Reina et al. |
| 9,561,095 B1 | 2/2017 | Nguyen |
| 9,561,446 B2 | 2/2017 | Brecher |
| 9,565,415 B2 | 2/2017 | Zhang et al. |
| 9,572,661 B2 | 2/2017 | Robin |
| 9,576,398 B1 | 2/2017 | Zehner et al. |
| 9,576,556 B2 | 2/2017 | Simmons |
| 9,581,822 B2 | 2/2017 | Morimoto |
| 9,610,056 B2 | 4/2017 | Lavallee et al. |
| 9,612,657 B2 | 4/2017 | Bertram et al. |
| 9,626,936 B2 | 4/2017 | Bell |
| 9,629,595 B2 | 4/2017 | Walker |
| 9,633,431 B2 | 4/2017 | Merlet |
| 9,645,395 B2 | 5/2017 | Bolas et al. |
| 9,646,423 B1 | 5/2017 | Sun et al. |
| 9,672,597 B2 | 6/2017 | Amiot |
| 9,672,607 B2 | 6/2017 | Demri et al. |
| 9,672,640 B2 | 6/2017 | Kleiner |
| 9,675,306 B2 | 6/2017 | Morton |
| 9,675,319 B1 | 6/2017 | Razzaque |
| 9,684,980 B2 | 6/2017 | Royalty et al. |
| 9,690,119 B2 | 6/2017 | Garofolo et al. |
| RE46,463 E | 7/2017 | Feinbloom |
| 9,693,748 B2 | 7/2017 | Rai et al. |
| 9,710,968 B2 | 7/2017 | Dillavou et al. |
| 9,713,502 B2 | 7/2017 | Finkman |
| 9,724,119 B2 | 8/2017 | Hissong |
| 9,724,165 B2 | 8/2017 | Arata et al. |
| 9,726,888 B2 | 8/2017 | Giartisio |
| 9,728,006 B2 | 8/2017 | Varga |
| 9,729,831 B2 | 8/2017 | Birnkrant |
| 9,746,739 B2 | 8/2017 | Alton et al. |
| 9,757,034 B2 | 9/2017 | Desjardins |
| 9,757,087 B2 | 9/2017 | Simon et al. |
| 9,766,441 B2 | 9/2017 | Rappel |
| 9,766,459 B2 | 9/2017 | Alton et al. |
| 9,767,608 B2 | 9/2017 | Lee et al. |
| 9,770,203 B1 | 9/2017 | Berme |
| 9,772,102 B1 | 9/2017 | Ferguson |
| 9,772,495 B2 | 9/2017 | Tam |
| 9,791,138 B1 | 10/2017 | Feinbloom |
| 9,800,995 B2 | 10/2017 | Libin |
| 9,805,504 B2 | 10/2017 | Zhang |
| 9,808,148 B2 | 11/2017 | Miller |
| 9,839,448 B2 | 12/2017 | Reckling et al. |
| 9,844,413 B2 | 12/2017 | Daon et al. |
| 9,851,080 B2 | 12/2017 | Wilt |
| 9,858,663 B2 | 1/2018 | Penney et al. |
| 9,861,446 B2 | 1/2018 | Lang |
| 9,864,214 B2 | 1/2018 | Fass |
| 9,872,733 B2 | 1/2018 | Shoham et al. |
| 9,875,544 B2 | 1/2018 | Rai et al. |
| 9,877,642 B2 | 1/2018 | Duret |
| 9,885,465 B2 | 2/2018 | Nguyen |
| 9,886,552 B2 | 2/2018 | Dillavou et al. |
| 9,886,760 B2 | 2/2018 | Liu et al. |
| 9,892,564 B1 | 2/2018 | Cvetko et al. |
| 9,898,866 B2 | 2/2018 | Fuchs et al. |
| 9,901,414 B2 | 2/2018 | Lively |
| 9,911,187 B2 | 3/2018 | Steinle |
| 9,911,236 B2 | 3/2018 | Bar et al. |
| 9,927,611 B2 | 3/2018 | Rudy |
| 9,928,629 B2 | 3/2018 | Benishti et al. |
| 9,940,750 B2 | 4/2018 | Dillavou et al. |
| 9,943,374 B2 | 4/2018 | Merritt et al. |
| 9,947,110 B2 | 4/2018 | Haimerl |
| 9,952,664 B2 | 4/2018 | Border et al. |
| 9,956,054 B2 | 5/2018 | Aguirre-Valencia |
| 9,958,674 B2 | 5/2018 | Border |
| 9,959,620 B2 | 5/2018 | Merlet |
| 9,959,629 B2 | 5/2018 | Dillavou et al. |
| 9,965,681 B2 | 5/2018 | Border et al. |
| 9,968,297 B2 | 5/2018 | Connor |
| 9,980,780 B2 | 5/2018 | Lang |
| 9,986,228 B2 | 5/2018 | Woods |
| D824,523 S | 7/2018 | Paoli et al. |
| 10,010,379 B1 | 7/2018 | Gibby et al. |
| 10,013,531 B2 | 7/2018 | Richards |
| 10,015,243 B2 | 7/2018 | Kazerani et al. |
| 10,016,243 B2 | 7/2018 | Esterberg |
| 10,022,064 B2 | 7/2018 | Kim et al. |

(56) References Cited

U.S. PATENT DOCUMENTS

| | | | |
|---|---|---|---|
| 10,022,065 B2 | 7/2018 | Yishai et al. |
| 10,022,104 B2 | 7/2018 | Sell et al. |
| 10,023,615 B2 | 7/2018 | Bonny |
| 10,026,015 B2 | 7/2018 | Cavusoglu |
| 10,034,713 B2 | 7/2018 | Yang et al. |
| 10,042,167 B2 | 8/2018 | McDowall et al. |
| 10,046,165 B2 | 8/2018 | Frewin |
| 10,055,838 B2 | 8/2018 | Elenbaas et al. |
| 10,066,816 B2 | 9/2018 | Chang |
| 10,067,359 B1 | 9/2018 | Ushakov |
| 10,073,515 B2 | 9/2018 | Awdeh |
| 10,080,616 B2 | 9/2018 | Wilkinson et al. |
| 10,082,680 B2 | 9/2018 | Chang |
| 10,085,709 B2 | 10/2018 | Lavallee et al. |
| 10,105,187 B2 | 10/2018 | Corndorf et al. |
| 10,107,483 B2 | 10/2018 | Oren |
| 10,108,833 B2 | 10/2018 | Hong et al. |
| 10,123,840 B2 | 11/2018 | Dorman |
| 10,130,378 B2 | 11/2018 | Bryan |
| 10,132,483 B1 | 11/2018 | Feinbloom |
| 10,134,166 B2 | 11/2018 | Benishti et al. |
| 10,134,194 B2 | 11/2018 | Kepner |
| 10,139,652 B2 | 11/2018 | Windham |
| 10,139,920 B2 | 11/2018 | Isaacs |
| 10,142,496 B1 | 11/2018 | Rao |
| 10,151,928 B2 | 12/2018 | Ushakov |
| 10,154,239 B2 | 12/2018 | Casas |
| 10,159,530 B2 | 12/2018 | Lang |
| 10,163,207 B2 | 12/2018 | Merlet |
| 10,166,079 B2 | 1/2019 | McLachlin et al. |
| 10,175,507 B2 | 1/2019 | Nakamura |
| 10,175,753 B2 | 1/2019 | Boesen |
| 10,181,361 B2 | 1/2019 | Pillavou et al. |
| 10,186,055 B2 | 1/2019 | Takahashi |
| 10,188,672 B2 | 1/2019 | Wagner |
| 10,194,131 B2 | 1/2019 | Casas |
| 10,194,990 B2 | 2/2019 | Amanatullah et al. |
| 10,194,993 B2 | 2/2019 | Roger et al. |
| 10,195,076 B2 | 2/2019 | Fateh |
| 10,197,803 B2 | 2/2019 | Badiali et al. |
| 10,197,816 B2 | 2/2019 | Waisman |
| 10,207,315 B2 | 2/2019 | Appleby |
| 10,212,517 B1 | 2/2019 | Beltran et al. |
| 10,230,719 B2 | 3/2019 | Vaugn |
| 10,231,893 B2 | 3/2019 | Lei |
| 10,235,606 B2 | 3/2019 | Miao |
| 10,240,769 B1 | 3/2019 | Braganca |
| 10,247,965 B2 | 4/2019 | Ton |
| 10,251,724 B2 | 4/2019 | McLachlin et al. |
| 10,261,324 B2 | 4/2019 | Chuang et al. |
| 10,262,424 B2 | 4/2019 | Ketcha et al. |
| 10,274,731 B2 | 4/2019 | Maimone |
| 10,278,777 B1 | 5/2019 | Lang |
| 10,292,768 B2 | 5/2019 | Lang |
| 10,296,805 B2 | 5/2019 | Yang et al. |
| 10,319,154 B1 | 6/2019 | Chakravarthula et al. |
| 10,326,975 B2 | 6/2019 | Casas |
| 10,332,267 B2 | 6/2019 | Rai et al. |
| 10,339,719 B2 | 7/2019 | Jagga et al. |
| 10,352,543 B1 | 7/2019 | Braganca |
| 10,357,146 B2 | 7/2019 | Fiebel |
| 10,357,574 B2 | 7/2019 | Hilderbrand |
| 10,366,489 B2 | 7/2019 | Boettger et al. |
| 10,368,947 B2 | 8/2019 | Lang |
| 10,368,948 B2 | 8/2019 | Tripathi |
| 10,382,748 B2 | 8/2019 | Benishti et al. |
| 10,383,654 B2 | 8/2019 | Yilmaz et al. |
| 10,386,645 B2 | 8/2019 | Shousha |
| 10,388,076 B2 | 8/2019 | Bar-Zeev et al. |
| 10,398,514 B2 | 9/2019 | Ryan et al. |
| 10,401,657 B2 | 9/2019 | Jiang et al. |
| 10,405,825 B2 | 9/2019 | Rai et al. |
| 10,405,927 B1 | 9/2019 | Lang |
| 10,413,752 B2 | 9/2019 | Berlinger et al. |
| 10,419,655 B2 | 9/2019 | Sivan |
| 10,420,626 B2 | 9/2019 | Tokuda et al. |
| 10,420,813 B2 | 9/2019 | Newell-Rogers |
| 10,424,115 B2 | 9/2019 | Ellerbrock |
| D862,469 S | 10/2019 | Sadot et al. |
| 10,426,554 B2 | 10/2019 | Siewerdsen et al. |
| 10,429,675 B2 | 10/2019 | Greget |
| 10,431,008 B2 | 10/2019 | Djajadiningrat |
| 10,433,814 B2 | 10/2019 | Razzaque |
| 10,434,335 B2 | 10/2019 | Takahashi |
| 10,441,236 B2 | 10/2019 | Bar-Tal et al. |
| 10,444,514 B2 | 10/2019 | Abou Shousha et al. |
| 10,447,947 B2 | 10/2019 | Liu |
| 10,448,003 B2 | 10/2019 | Grafenberg |
| 10,449,040 B2 | 10/2019 | Lashinski |
| 10,453,187 B2 | 10/2019 | Peterson |
| 10,463,434 B2 | 11/2019 | Siegler et al. |
| 10,465,892 B1 | 11/2019 | Feinbloom |
| 10,466,487 B2 | 11/2019 | Blum et al. |
| 10,470,732 B2 | 11/2019 | Baumgart |
| 10,473,314 B1 | 11/2019 | Braganca |
| 10,485,989 B2 | 11/2019 | Jordan |
| 10,488,663 B2 | 11/2019 | Choi |
| D869,772 S | 12/2019 | Gand |
| D870,977 S | 12/2019 | Berggren et al. |
| 10,492,755 B2 | 12/2019 | Lin et al. |
| 10,499,997 B2 | 12/2019 | Weinstein et al. |
| 10,502,363 B2 | 12/2019 | Edwards et al. |
| 10,504,231 B2 | 12/2019 | Fiala |
| 10,507,066 B2 | 12/2019 | DiMaio |
| 10,511,822 B2 | 12/2019 | Casas |
| 10,517,544 B2 | 12/2019 | Taguchi |
| 10,537,395 B2 | 1/2020 | Perez |
| 10,540,780 B1 | 1/2020 | Cousins |
| 10,543,485 B2 | 1/2020 | Ismagilov |
| 10,546,423 B2 | 1/2020 | Jones et al. |
| 10,548,557 B2 | 2/2020 | Lim |
| 10,555,775 B2 | 2/2020 | Hoffman |
| 10,568,535 B2 | 2/2020 | Roberts et al. |
| 10,571,696 B2 | 2/2020 | Urey et al. |
| 10,571,716 B2 | 2/2020 | Chapiro |
| 10,573,086 B2 | 2/2020 | Bar-Zeev et al. |
| 10,573,087 B2 | 2/2020 | Gallop |
| 10,602,114 B2 | 2/2020 | Casas |
| 10,577,630 B2 | 3/2020 | Zhang |
| 10,586,400 B2 | 3/2020 | Douglas |
| 10,591,737 B2 | 3/2020 | Yildiz et al. |
| 10,592,748 B1 | 3/2020 | Cousins |
| 10,595,716 B2 | 3/2020 | Nazareth |
| 10,601,950 B2 | 3/2020 | Devam et al. |
| 10,603,113 B2 | 3/2020 | Lang |
| 10,603,133 B2 | 3/2020 | Wang et al. |
| 10,606,085 B2 | 3/2020 | Toyama |
| 10,594,998 B1 | 4/2020 | Casas |
| 10,610,172 B2 | 4/2020 | Hummel et al. |
| 10,610,179 B2 | 4/2020 | Altmann |
| 10,613,352 B2 | 4/2020 | Knoll |
| 10,617,566 B2 | 4/2020 | Esmonde |
| 10,620,460 B2 | 4/2020 | Carabin |
| 10,621,738 B2 | 4/2020 | Miao et al. |
| 10,625,099 B2 | 4/2020 | Takahashi |
| 10,626,473 B2 | 4/2020 | Mariani |
| 10,631,905 B2 | 4/2020 | Asfora et al. |
| 10,631,907 B2 | 4/2020 | Zucker |
| 10,634,331 B1 | 4/2020 | Feinbloom |
| 10,634,921 B2 | 4/2020 | Blum et al. |
| 10,638,080 B2 | 4/2020 | Ovchinnikov |
| 10,646,285 B2 | 5/2020 | Siemionow et al. |
| 10,650,513 B2 | 5/2020 | Penney et al. |
| 10,650,594 B2 | 5/2020 | Jones |
| 10,652,525 B2 | 5/2020 | Woods |
| 10,653,495 B2 | 5/2020 | Gregerson et al. |
| 10,660,715 B2 | 5/2020 | Dozeman |
| 10,663,738 B2 | 5/2020 | Carlvik |
| 10,665,033 B2 | 5/2020 | Bar-Zeev et al. |
| 10,670,937 B2 | 6/2020 | Alton et al. |
| 10,672,145 B2 | 6/2020 | Albiol et al. |
| 10,682,112 B2 | 6/2020 | Pizaine |
| 10,682,767 B2 | 6/2020 | Grafenberg et al. |
| 10,687,901 B2 | 6/2020 | Thomas |

(56) References Cited

U.S. PATENT DOCUMENTS

| | | |
|---|---|---|
| 10,691,397 B1 | 6/2020 | Clements |
| 10,702,713 B2 | 7/2020 | Mori |
| 10,706,540 B2 | 7/2020 | Merlet |
| 10,709,398 B2 | 7/2020 | Schweizer |
| 10,713,801 B2 | 7/2020 | Jordan |
| 10,716,643 B2 | 7/2020 | Justin et al. |
| 10,722,733 B2 | 7/2020 | Takahashi |
| 10,725,535 B2 | 7/2020 | Yu |
| 10,731,832 B2 | 8/2020 | Koo |
| 10,732,721 B1 | 8/2020 | Clements |
| 10,742,949 B2 | 8/2020 | Casas |
| 10,743,939 B1 | 8/2020 | Lang |
| 10,743,943 B2 | 8/2020 | Razeto et al. |
| 10,747,315 B2 | 8/2020 | Tungare |
| 10,748,319 B1 | 8/2020 | Tao et al. |
| 10,758,315 B2 | 9/2020 | Johnson et al. |
| 10,777,094 B1 | 9/2020 | Rao |
| 10,777,315 B2 | 9/2020 | Zehavi |
| 10,781,482 B2 | 9/2020 | Gubatayao |
| 10,792,110 B2 | 10/2020 | Leung et al. |
| 10,799,145 B2 | 10/2020 | Found |
| 10,799,296 B2 | 10/2020 | Lang |
| 10,799,298 B2 | 10/2020 | Crawford et al. |
| 10,799,316 B2 | 10/2020 | Sela et al. |
| 10,810,799 B2 | 10/2020 | Tepper et al. |
| 10,818,019 B2 | 10/2020 | Piat |
| 10,818,101 B2 | 10/2020 | Gallop et al. |
| 10,818,199 B2 | 10/2020 | Buras et al. |
| 10,825,563 B2 | 11/2020 | Gibby et al. |
| 10,827,164 B2 | 11/2020 | Perreault et al. |
| 10,831,943 B2 | 11/2020 | Santarone |
| 10,835,296 B2 | 11/2020 | Elimelech |
| 10,838,206 B2 | 11/2020 | Fortin-Deschenes et al. |
| 10,839,629 B2 | 11/2020 | Jones |
| 10,839,956 B2 | 11/2020 | Beydoun et al. |
| 10,841,556 B2 | 11/2020 | Casas |
| 10,842,002 B2 | 11/2020 | Chang |
| 10,842,461 B2 | 11/2020 | Johnson et al. |
| 10,849,691 B2 | 12/2020 | Zucker |
| 10,849,693 B2 | 12/2020 | Lang |
| 10,849,710 B2 | 12/2020 | Liu |
| 10,861,236 B2 | 12/2020 | Geri et al. |
| 10,865,220 B2 | 12/2020 | Ebetino |
| 10,869,517 B1 | 12/2020 | Halpern |
| 10,869,727 B2 | 12/2020 | Yanof et al. |
| 10,872,472 B2 | 12/2020 | Watola |
| 10,877,262 B1 | 12/2020 | Luxembourg |
| 10,877,296 B2 | 12/2020 | Lindsey |
| 10,878,639 B2 | 12/2020 | Douglas |
| 10,893,260 B2 | 1/2021 | Trail et al. |
| 10,895,742 B2 | 1/2021 | Schneider |
| 10,895,743 B2 | 1/2021 | Dausmann |
| 10,895,906 B2 | 1/2021 | West et al. |
| 10,898,151 B2 | 1/2021 | Harding et al. |
| 10,908,420 B2 | 2/2021 | Lee et al. |
| 10,921,595 B2 | 2/2021 | Rakshit |
| 10,921,613 B2 | 2/2021 | Gupta et al. |
| 10,928,321 B2 | 2/2021 | Rawle |
| 10,928,638 B2 | 2/2021 | Ninan |
| 10,929,670 B1 | 2/2021 | Troy et al. |
| 10,935,815 B1 | 3/2021 | Castaneda |
| 10,935,816 B2 | 3/2021 | Ban |
| 10,936,537 B2 | 3/2021 | Huston |
| 10,939,973 B2 | 3/2021 | DiMaio |
| 10,939,977 B2 | 3/2021 | Messinger et al. |
| 10,941,933 B2 | 3/2021 | Ferguson |
| 10,946,108 B2 | 3/2021 | Zhang |
| 10,950,338 B2 | 3/2021 | Douglas |
| 10,951,872 B2 | 3/2021 | Casas |
| 10,964,095 B1 | 3/2021 | Douglas |
| 10,964,124 B1 | 3/2021 | Douglas |
| 10,966,768 B2 | 4/2021 | Poulos |
| 10,969,587 B2 | 4/2021 | McDowall et al. |
| 10,993,754 B2 | 5/2021 | Kuntz et al. |
| 11,000,335 B2 | 5/2021 | Dorman |
| 11,002,994 B2 | 5/2021 | Jiang et al. |
| 11,006,093 B1 | 5/2021 | Hegyi |
| 11,013,550 B2 | 5/2021 | Rioux et al. |
| 11,013,560 B2 | 5/2021 | Lang |
| 11,013,562 B2 | 5/2021 | Marti |
| 11,013,573 B2 | 5/2021 | Chang |
| 11,013,900 B2 | 5/2021 | Malek |
| 11,016,302 B2 | 5/2021 | Freeman et al. |
| 11,019,988 B2 | 6/2021 | Fiebel |
| 11,027,027 B2 | 6/2021 | Manning |
| 11,029,147 B2 | 6/2021 | Abovitz et al. |
| 11,030,809 B2 | 6/2021 | Wang |
| 11,041,173 B2 | 6/2021 | Zhang |
| 11,045,663 B2 | 6/2021 | Mori |
| 11,049,293 B2 | 6/2021 | Chae |
| 11,049,476 B2 | 6/2021 | Fuchs et al. |
| 11,050,990 B2 | 6/2021 | Casas |
| 11,057,505 B2 | 7/2021 | Dharmatilleke |
| 11,058,390 B1 | 7/2021 | Douglas |
| 11,061,257 B1 | 7/2021 | Hakim |
| 11,064,904 B2 | 7/2021 | Kay et al. |
| 11,065,062 B2 | 7/2021 | Frushour |
| 11,067,387 B2 | 7/2021 | Marell |
| 11,071,497 B2 | 7/2021 | Hallack |
| 11,079,596 B2 | 8/2021 | Hua et al. |
| 11,087,039 B2 | 8/2021 | Duff |
| 11,090,019 B2 | 8/2021 | Siemionow et al. |
| 11,097,129 B2 | 8/2021 | Sakata |
| 11,099,376 B1 | 8/2021 | Steier |
| 11,103,320 B2 | 8/2021 | LeBoeuf |
| D930,162 S | 9/2021 | Cremer et al. |
| 11,109,762 B1 | 9/2021 | Steier |
| 11,112,611 B1 | 9/2021 | Kessler et al. |
| 11,122,164 B2 | 9/2021 | Gigante |
| 11,123,604 B2 | 9/2021 | Fung |
| 11,129,562 B2 | 9/2021 | Roberts et al. |
| 11,132,055 B2 | 9/2021 | Jones et al. |
| 11,135,015 B2 | 10/2021 | Crawford |
| 11,135,016 B2 | 10/2021 | Frielinghaus et al. |
| 11,137,610 B1 | 10/2021 | Kessler et al. |
| 11,141,221 B2 | 10/2021 | Hobeika |
| 11,153,549 B2 | 10/2021 | Casas |
| 11,153,555 B1 | 11/2021 | Healy et al. |
| 11,163,176 B2 | 11/2021 | Karafin |
| 11,164,324 B2 | 11/2021 | Liu |
| 11,166,006 B2 | 11/2021 | Hegyi |
| 11,169,380 B2 | 11/2021 | Manly et al. |
| 11,172,990 B2 | 11/2021 | Lang |
| 11,179,136 B2 | 11/2021 | Kohli |
| 11,180,557 B2 | 11/2021 | Noelle |
| 11,181,747 B1 | 11/2021 | Kessler et al. |
| 11,185,891 B2 | 11/2021 | Cousins |
| 11,187,907 B2 | 11/2021 | Osterman et al. |
| 11,202,682 B2 | 12/2021 | Staunton |
| 11,207,150 B2 | 12/2021 | Healy |
| 11,217,028 B2 | 1/2022 | Jones |
| 11,224,483 B2 | 1/2022 | Steinberg et al. |
| 11,224,763 B2 | 1/2022 | Takahashi |
| 11,227,417 B2 | 1/2022 | Berlinger |
| 11,231,787 B2 | 1/2022 | Isaacs et al. |
| 11,243,404 B2 | 2/2022 | McDowall et al. |
| 11,244,508 B2 | 2/2022 | Kazanzides et al. |
| 11,253,216 B2 | 2/2022 | Crawford et al. |
| 11,253,323 B2 | 2/2022 | Hughes et al. |
| 11,257,190 B2 | 2/2022 | Mao |
| 11,257,241 B2 | 2/2022 | Tao |
| 11,263,772 B2 | 3/2022 | Siemionow et al. |
| 11,269,401 B2 | 3/2022 | West et al. |
| 11,272,151 B2 | 3/2022 | Casas |
| 11,278,359 B2 | 3/2022 | Siemionow et al. |
| 11,278,413 B1 | 3/2022 | Lang |
| 11,280,480 B2 | 3/2022 | Wilt |
| 11,284,846 B2 | 3/2022 | Graumann |
| 11,311,341 B2 | 3/2022 | Lang |
| 11,291,521 B2 | 4/2022 | Im |
| 11,294,167 B2 | 4/2022 | Ishimoda |
| 11,297,285 B2 | 4/2022 | Pierce |
| 11,300,252 B2 | 4/2022 | Nguyen |
| 11,300,790 B2 | 4/2022 | Cheng et al. |

(56) References Cited

U.S. PATENT DOCUMENTS

| | | |
|---|---|---|
| 11,304,621 B2 | 4/2022 | Merschon et al. |
| 11,304,759 B2 | 4/2022 | Kovtun et al. |
| 11,307,402 B2 | 4/2022 | Steier |
| 11,308,663 B2 | 4/2022 | Alhrishy et al. |
| 11,317,973 B2 | 5/2022 | Calloway |
| 11,337,763 B2 | 5/2022 | Choi |
| 11,348,257 B2 | 5/2022 | Lang |
| 11,350,072 B1 | 5/2022 | Casas |
| 11,350,965 B2 | 6/2022 | Yilmaz et al. |
| 11,351,006 B2 | 6/2022 | Aferzon |
| 11,354,813 B2 | 6/2022 | Piat et al. |
| 11,360,315 B2 | 6/2022 | Tu |
| 11,373,342 B2 | 6/2022 | Stafford et al. |
| 11,382,699 B2 | 7/2022 | Wassall |
| 11,382,700 B2 | 7/2022 | Calloway |
| 11,382,712 B2 | 7/2022 | Elimelech et al. |
| 11,382,713 B2 | 7/2022 | Healy |
| 11,389,252 B2 | 7/2022 | Gera et al. |
| 11,393,229 B2 | 7/2022 | Zhou et al. |
| 11,399,895 B2 | 8/2022 | Soper et al. |
| 11,402,524 B2 | 8/2022 | Song et al. |
| 11,406,338 B2 | 8/2022 | Tolkowsky |
| 11,412,202 B2 | 8/2022 | Hegyi |
| 11,423,554 B2 | 8/2022 | Borsdorf et al. |
| 11,430,203 B2 | 8/2022 | Navab et al. |
| 11,432,828 B1 | 9/2022 | Lang |
| 11,432,931 B2 | 9/2022 | Lang |
| 11,443,428 B2 | 9/2022 | Petersen et al. |
| 11,443,431 B2 | 9/2022 | Flossmann et al. |
| 11,452,568 B2 | 9/2022 | Lang |
| 11,452,570 B2 | 9/2022 | Tolkowsky |
| 11,460,915 B2 | 10/2022 | Frielinghaus |
| 11,461,936 B2 | 10/2022 | Freeman et al. |
| 11,461,983 B2 | 10/2022 | Jones |
| 11,464,580 B2 | 10/2022 | Kemp et al. |
| 11,464,581 B2 | 10/2022 | Calloway |
| 11,475,625 B1 | 10/2022 | Douglas |
| 11,478,214 B2 | 10/2022 | Siewerdsen et al. |
| 11,483,532 B2 | 10/2022 | Casas |
| 11,488,021 B2 | 11/2022 | Sun et al. |
| 11,490,986 B2 | 11/2022 | BEn-Yishai |
| 11,510,750 B2 | 11/2022 | Dulin et al. |
| 11,513,358 B2 | 11/2022 | McDowall et al. |
| 11,527,002 B2 | 12/2022 | Govari |
| 11,528,393 B2 | 12/2022 | Garofolo et al. |
| 11,544,031 B2 | 1/2023 | Harviainen |
| 11,573,420 B2 | 2/2023 | Sarma et al. |
| 11,589,927 B2 | 2/2023 | Oezbek et al. |
| 11,627,924 B2 | 4/2023 | Alexandroni et al. |
| 11,644,675 B2 | 5/2023 | Manly et al. |
| 11,648,016 B2 | 5/2023 | Hathaway et al. |
| 11,651,499 B2 | 5/2023 | Wang et al. |
| 11,657,518 B2 | 5/2023 | Ketcha et al. |
| 11,666,458 B2 | 6/2023 | Kim et al. |
| 11,669,984 B2 | 6/2023 | Siewerdsen et al. |
| 11,686,947 B2 | 6/2023 | Loyola et al. |
| 11,699,236 B2 | 7/2023 | Avital et al. |
| 11,712,582 B2 | 8/2023 | Miyazaki et al. |
| 11,715,210 B2 | 8/2023 | Haslam et al. |
| 11,719,941 B2 | 8/2023 | Russell |
| 11,730,389 B2 | 8/2023 | Farshad et al. |
| 11,733,516 B2 | 8/2023 | Edwin et al. |
| 11,734,901 B2 | 8/2023 | Jones et al. |
| 11,744,657 B2 | 9/2023 | Leboeuf et al. |
| 11,750,794 B2 | 9/2023 | Benishti et al. |
| 11,766,296 B2 | 9/2023 | Wolf et al. |
| 11,798,178 B2 | 10/2023 | Merlet |
| 11,801,097 B2 | 10/2023 | Crawford et al. |
| 11,801,115 B2 | 10/2023 | Elimelech et al. |
| 11,808,943 B2 | 11/2023 | Robaina et al. |
| 11,815,683 B2 | 11/2023 | Sears et al. |
| 11,826,111 B2 | 11/2023 | Mahfouz |
| 11,832,886 B2 | 12/2023 | Dorman |
| 11,838,493 B2 | 12/2023 | Healy et al. |
| 11,839,433 B2 | 12/2023 | Schaewe et al. |
| 11,839,501 B2 | 12/2023 | Takahashi et al. |
| 11,864,934 B2 | 1/2024 | Junio et al. |
| 11,885,752 B2 | 1/2024 | St-Aubin et al. |
| 11,892,647 B2 | 2/2024 | Hung et al. |
| 11,896,445 B2 | 2/2024 | Gera et al. |
| 11,900,620 B2 | 2/2024 | Lalys et al. |
| 11,914,155 B2 | 2/2024 | Zhu et al. |
| 11,918,310 B1 | 3/2024 | Roh et al. |
| 11,922,631 B2 | 3/2024 | Haslam et al. |
| 11,941,814 B2 | 3/2024 | Crawford et al. |
| 11,944,508 B1 | 4/2024 | Cowin et al. |
| 11,948,265 B2 | 4/2024 | Gibby et al. |
| 11,950,968 B2 | 4/2024 | Wiggermann |
| 11,957,420 B2 | 4/2024 | Lang |
| 11,961,193 B2 | 4/2024 | Pelzl et al. |
| 11,963,723 B2 | 4/2024 | Vilsmeier et al. |
| 11,972,582 B2 | 4/2024 | Yan et al. |
| 11,974,819 B2 | 5/2024 | Finley et al. |
| 11,974,887 B2 | 5/2024 | Elimelech et al. |
| 11,977,232 B2 | 5/2024 | Wu et al. |
| 11,980,429 B2 | 5/2024 | Wolf et al. |
| 11,980,506 B2 | 5/2024 | Wolf et al. |
| 11,980,507 B2 | 5/2024 | Elimelech et al. |
| 11,980,508 B2 | 5/2024 | Elimelech et al. |
| 11,983,824 B2 | 5/2024 | Avisar et al. |
| 12,002,171 B2 | 6/2024 | Jones et al. |
| 12,010,285 B2 | 6/2024 | Quiles Casas |
| 12,014,497 B2 | 6/2024 | Hong et al. |
| 12,019,314 B1 | 6/2024 | Steines et al. |
| 12,033,322 B2 | 7/2024 | Laaksonen et al. |
| 12,044,856 B2 | 7/2024 | Gera et al. |
| 12,044,858 B2 | 7/2024 | Gera et al. |
| 12,056,830 B2 | 8/2024 | Cvetko et al. |
| 12,059,281 B2 | 8/2024 | Weingarten et al. |
| 12,063,338 B2 | 8/2024 | Quiles Casas |
| 12,063,345 B2 | 8/2024 | Benishti et al. |
| 12,069,233 B2 | 8/2024 | Benishti et al. |
| 12,076,158 B2 | 9/2024 | Geiger et al. |
| 12,076,196 B2 | 9/2024 | Elimelech et al. |
| 12,079,385 B2 | 9/2024 | Ben-Yishai et al. |
| 2002/0082498 A1 | 6/2002 | Wendt et al. |
| 2003/0059097 A1 | 3/2003 | Abovitz et al. |
| 2003/0117393 A1 | 6/2003 | Sauer et al. |
| 2003/0130576 A1 | 7/2003 | Seeley |
| 2003/0156144 A1 | 8/2003 | Morita |
| 2003/0210812 A1 | 11/2003 | Khamene et al. |
| 2003/0225329 A1 | 12/2003 | Rossner et al. |
| 2004/0019263 A1 | 1/2004 | Jutras et al. |
| 2004/0030237 A1 | 2/2004 | Lee et al. |
| 2004/0138556 A1 | 7/2004 | Cosman |
| 2004/0152955 A1 | 8/2004 | McGinley et al. |
| 2004/0171930 A1 | 9/2004 | Grimm et al. |
| 2005/0017972 A1 | 1/2005 | Poole |
| 2005/0024586 A1 | 2/2005 | Teiwes et al. |
| 2005/0119639 A1 | 6/2005 | McCombs et al. |
| 2005/0154296 A1 | 7/2005 | Lechner et al. |
| 2005/0203367 A1 | 9/2005 | Ahmed et al. |
| 2005/0203380 A1 | 9/2005 | Sauer et al. |
| 2005/0215879 A1 | 9/2005 | Chuanggui |
| 2005/0267358 A1 | 12/2005 | Tuma et al. |
| 2006/0072124 A1 | 4/2006 | Smetak et al. |
| 2006/0134198 A1 | 6/2006 | Tawa |
| 2006/0147100 A1 | 7/2006 | Fitzpatrick |
| 2006/0176242 A1 | 8/2006 | Jaramaz et al. |
| 2007/0018975 A1 | 1/2007 | Chaunggui et al. |
| 2007/0058261 A1 | 3/2007 | Sugihara et al. |
| 2007/0100325 A1 | 5/2007 | Jutras et al. |
| 2007/0233371 A1 | 10/2007 | Stoschek et al. |
| 2008/0007645 A1 | 1/2008 | McCutchen |
| 2008/0035266 A1 | 2/2008 | Danziger |
| 2008/0085033 A1 | 4/2008 | Haven et al. |
| 2008/0159612 A1 | 7/2008 | Fu |
| 2008/0183065 A1 | 7/2008 | Goldbach |
| 2008/0221625 A1 | 9/2008 | Hufner et al. |
| 2008/0253527 A1 | 10/2008 | Boyden et al. |
| 2008/0262812 A1 | 10/2008 | Arata et al. |
| 2008/0287728 A1 | 11/2008 | Mostafavi et al. |
| 2009/0005961 A1 | 1/2009 | Grabowski et al. |
| 2009/0018437 A1 | 1/2009 | Cooke |

(56) References Cited

U.S. PATENT DOCUMENTS

| | | |
|---|---|---|
| 2009/0024127 A1 | 1/2009 | Lechner et al. |
| 2009/0036902 A1 | 2/2009 | Dimaio et al. |
| 2009/0062869 A1 | 3/2009 | Claverie et al. |
| 2009/0099445 A1 | 4/2009 | Burger |
| 2009/0227847 A1 | 9/2009 | Tepper et al. |
| 2009/0285366 A1 | 11/2009 | Essenreiter et al. |
| 2009/0300540 A1 | 12/2009 | Russell |
| 2010/0076305 A1 | 3/2010 | Maier-Hein et al. |
| 2010/0094308 A1 | 4/2010 | Tatsumi et al. |
| 2010/0106010 A1 | 4/2010 | Rubner et al. |
| 2010/0114110 A1 | 5/2010 | Taft et al. |
| 2010/0149073 A1 | 6/2010 | Chaum et al. |
| 2010/0172567 A1 | 7/2010 | Prokoski |
| 2010/0210939 A1 | 8/2010 | Hartmann et al. |
| 2010/0266220 A1 | 10/2010 | Zagorchev et al. |
| 2010/0274124 A1 | 10/2010 | Jascob et al. |
| 2011/0004259 A1 | 1/2011 | Stallings et al. |
| 2011/0098553 A1 | 4/2011 | Robbins et al. |
| 2011/0105895 A1 | 5/2011 | Kornblau et al. |
| 2011/0216060 A1 | 9/2011 | Weising et al. |
| 2011/0245625 A1 | 10/2011 | Trovato et al. |
| 2011/0248064 A1 | 10/2011 | Marczyk |
| 2011/0254922 A1 | 10/2011 | Schaerer et al. |
| 2011/0306873 A1 | 12/2011 | Shenai et al. |
| 2012/0014608 A1 | 1/2012 | Watanabe |
| 2012/0068913 A1 | 3/2012 | Bar-Zeev et al. |
| 2012/0078236 A1 | 3/2012 | Schoepp |
| 2012/0109151 A1 | 5/2012 | Maier-Hein et al. |
| 2012/0143050 A1 | 6/2012 | Heigl |
| 2012/0155064 A1 | 6/2012 | Waters |
| 2012/0162452 A1 | 6/2012 | Liu |
| 2012/0182605 A1 | 7/2012 | Hall et al. |
| 2012/0201421 A1 | 8/2012 | Hartmann et al. |
| 2012/0216411 A1 | 8/2012 | Wevers et al. |
| 2012/0224260 A1 | 9/2012 | Healy et al. |
| 2012/0289777 A1 | 11/2012 | Chopra et al. |
| 2012/0306850 A1 | 12/2012 | Balan et al. |
| 2012/0320100 A1 | 12/2012 | Machida et al. |
| 2013/0002928 A1 | 1/2013 | Imai |
| 2013/0009853 A1 | 1/2013 | Hesselink et al. |
| 2013/0038632 A1 | 2/2013 | Dillavou et al. |
| 2013/0050258 A1 | 2/2013 | Liu et al. |
| 2013/0050833 A1 | 2/2013 | Lewis et al. |
| 2013/0057581 A1 | 3/2013 | Meier |
| 2013/0079829 A1 | 3/2013 | Globerman et al. |
| 2013/0083009 A1 | 4/2013 | Geisner et al. |
| 2013/0106833 A1 | 5/2013 | Fun |
| 2013/0135734 A1 | 5/2013 | Shafer et al. |
| 2013/0135738 A1 | 5/2013 | Shafer et al. |
| 2013/0190602 A1 | 7/2013 | Liao |
| 2013/0195338 A1 | 8/2013 | Xu et al. |
| 2013/0209953 A1 | 8/2013 | Arlinsky et al. |
| 2013/0212453 A1 | 8/2013 | Gudai et al. |
| 2013/0234914 A1 | 9/2013 | Fujimaki |
| 2013/0234935 A1 | 9/2013 | Griffith |
| 2013/0237811 A1 | 9/2013 | Mihailescu et al. |
| 2013/0245461 A1 | 9/2013 | Maier-Hein et al. |
| 2013/0249787 A1 | 9/2013 | Morimoto |
| 2013/0249945 A1 | 9/2013 | Kobayashi |
| 2013/0265623 A1 | 10/2013 | Sugiyama et al. |
| 2013/0267838 A1 | 10/2013 | Fronk et al. |
| 2013/0278631 A1 | 10/2013 | Border et al. |
| 2013/0278635 A1 | 10/2013 | Maggiore |
| 2013/0300760 A1 | 11/2013 | Sugano et al. |
| 2013/0342571 A1 | 12/2013 | Kinnebrew et al. |
| 2013/0345718 A1 | 12/2013 | Crawford et al. |
| 2014/0031668 A1 | 1/2014 | Mobasser et al. |
| 2014/0049629 A1 | 2/2014 | Siewerdsen et al. |
| 2014/0088402 A1 | 3/2014 | Xu |
| 2014/0088990 A1 | 3/2014 | Nawana et al. |
| 2014/0104505 A1 | 4/2014 | Koenig |
| 2014/0114173 A1 | 4/2014 | Bar-Tal et al. |
| 2014/0142426 A1 | 5/2014 | Razzaque et al. |
| 2014/0168261 A1 | 6/2014 | Margolis et al. |
| 2014/0176661 A1 | 6/2014 | Smurro et al. |
| 2014/0177023 A1 | 6/2014 | Gao et al. |
| 2014/0189508 A1 | 7/2014 | Granchi et al. |
| 2014/0198129 A1 | 7/2014 | Liu et al. |
| 2014/0218291 A1 | 8/2014 | Kirk |
| 2014/0240484 A1 | 8/2014 | Kodama et al. |
| 2014/0243614 A1 | 8/2014 | Rothberg et al. |
| 2014/0256429 A1 | 9/2014 | Kobayashi et al. |
| 2014/0266983 A1 | 9/2014 | Christensen |
| 2014/0268356 A1 | 9/2014 | Bolas et al. |
| 2014/0270505 A1 | 9/2014 | Mccarthy |
| 2014/0275760 A1 | 9/2014 | Lee et al. |
| 2014/0285404 A1 | 9/2014 | Takano et al. |
| 2014/0285429 A1 | 9/2014 | Simmons |
| 2014/0300632 A1 | 10/2014 | Laor |
| 2014/0300967 A1 | 10/2014 | Tilleman et al. |
| 2014/0301624 A1 | 10/2014 | Barckow et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0336461 A1 | 11/2014 | Reiter |
| 2014/0340286 A1 | 11/2014 | Machida et al. |
| 2014/0361956 A1 | 12/2014 | Mikhailov et al. |
| 2014/0371728 A1 | 12/2014 | Vaughn |
| 2015/0005772 A1 | 1/2015 | Anglin et al. |
| 2015/0018672 A1 | 1/2015 | Blumhofer et al. |
| 2015/0031985 A1 | 1/2015 | Reddy et al. |
| 2015/0043798 A1 | 2/2015 | Carrell et al. |
| 2015/0070347 A1 | 3/2015 | Hofmann et al. |
| 2015/0084990 A1 | 3/2015 | Labor |
| 2015/0150641 A1 | 6/2015 | Daon et al. |
| 2015/0182293 A1* | 7/2015 | Yang ................. A61B 17/1703 600/424 |
| 2015/0209119 A1 | 7/2015 | Theodore et al. |
| 2015/0230873 A1 | 8/2015 | Kubiak et al. |
| 2015/0230893 A1 | 8/2015 | Huwais |
| 2015/0261922 A1 | 9/2015 | Nawana et al. |
| 2015/0277123 A1 | 10/2015 | Chaum et al. |
| 2015/0282735 A1 | 10/2015 | Rossner |
| 2015/0287188 A1 | 10/2015 | Gazit |
| 2015/0287236 A1 | 10/2015 | Winn |
| 2015/0297314 A1 | 10/2015 | Fowler et al. |
| 2015/0305828 A1 | 10/2015 | Park et al. |
| 2015/0310668 A1 | 10/2015 | Ellerbrock |
| 2015/0338652 A1 | 11/2015 | Lim et al. |
| 2015/0338653 A1 | 11/2015 | Subramaniam et al. |
| 2015/0350517 A1 | 12/2015 | Duret et al. |
| 2015/0351863 A1 | 12/2015 | Plassky et al. |
| 2015/0363978 A1 | 12/2015 | Maimone et al. |
| 2015/0366620 A1 | 12/2015 | Cameron et al. |
| 2016/0015878 A1 | 1/2016 | Graham et al. |
| 2016/0022287 A1 | 1/2016 | Nehls |
| 2016/0030131 A1 | 2/2016 | Yang et al. |
| 2016/0054571 A1 | 2/2016 | Tazbaz et al. |
| 2016/0086380 A1 | 3/2016 | Vayser et al. |
| 2016/0103318 A1 | 4/2016 | Du et al. |
| 2016/0125603 A1 | 5/2016 | Tanji |
| 2016/0133051 A1 | 5/2016 | Aonuma et al. |
| 2016/0143699 A1 | 5/2016 | Tanji |
| 2016/0153004 A1 | 6/2016 | Zhang |
| 2016/0163045 A1 | 6/2016 | Penney et al. |
| 2016/0175064 A1 | 6/2016 | Steinle et al. |
| 2016/0178910 A1 | 6/2016 | Giudicelli et al. |
| 2016/0191887 A1 | 6/2016 | Casas |
| 2016/0223822 A1 | 8/2016 | Harrison et al. |
| 2016/0246059 A1 | 8/2016 | Halpin et al. |
| 2016/0249989 A1 | 9/2016 | Devam et al. |
| 2016/0256223 A1 | 9/2016 | Haimerl et al. |
| 2016/0275684 A1 | 9/2016 | Elenbaas et al. |
| 2016/0297315 A1 | 10/2016 | Gonzalez et al. |
| 2016/0302870 A1 | 10/2016 | Wilkinson et al. |
| 2016/0324580 A1 | 11/2016 | Esterberg |
| 2016/0324583 A1 | 11/2016 | Kheradpir et al. |
| 2016/0339337 A1 | 11/2016 | Ellsworth et al. |
| 2017/0024634 A1 | 1/2017 | Miao et al. |
| 2017/0027650 A1 | 2/2017 | Merck et al. |
| 2017/0031163 A1 | 2/2017 | Gao et al. |
| 2017/0031179 A1 | 2/2017 | Guillot et al. |
| 2017/0045742 A1 | 2/2017 | Greenhalgh et al. |
| 2017/0065364 A1 | 3/2017 | Schuh et al. |

(56) References Cited

U.S. PATENT DOCUMENTS

| | | |
|---|---|---|
| 2017/0068119 A1 | 3/2017 | Antaki |
| 2017/0076501 A1 | 3/2017 | Jagga et al. |
| 2017/0086941 A1 | 3/2017 | Marti et al. |
| 2017/0112586 A1 | 4/2017 | Dhupar |
| 2017/0014119 A1 | 6/2017 | Capote et al. |
| 2017/0164919 A1 | 6/2017 | LaVallee et al. |
| 2017/0164920 A1 | 6/2017 | Lavallee et al. |
| 2017/0178375 A1 | 6/2017 | Benishti et al. |
| 2017/0220224 A1 | 8/2017 | Kodali |
| 2017/0239015 A1 | 8/2017 | Sela et al. |
| 2017/0245944 A1 | 8/2017 | Crawford et al. |
| 2017/0251900 A1 | 9/2017 | Hansen et al. |
| 2017/0252109 A1 | 9/2017 | Yang et al. |
| 2017/0258526 A1 | 9/2017 | Lang |
| 2017/0281283 A1 | 10/2017 | Siegler et al. |
| 2017/0312032 A1 | 11/2017 | Amanatullah et al. |
| 2017/0322950 A1 | 11/2017 | Han et al. |
| 2017/0348055 A1 | 12/2017 | Salcedo et al. |
| 2017/0348061 A1 | 12/2017 | Joshi et al. |
| 2017/0366773 A1 | 12/2017 | Kiraly et al. |
| 2017/0367766 A1 | 12/2017 | Mahfouz |
| 2017/0367771 A1 | 12/2017 | Tako et al. |
| 2017/0372477 A1 | 12/2017 | Penne |
| 2018/0003981 A1 | 1/2018 | Urey |
| 2018/0018791 A1 | 1/2018 | Guoyi |
| 2018/0021597 A1 | 1/2018 | Berlinger et al. |
| 2018/0028266 A1 | 2/2018 | Barnes et al. |
| 2018/0036884 A1 | 2/2018 | Chen et al. |
| 2018/0049622 A1 | 2/2018 | Ryan et al. |
| 2018/0055579 A1 | 3/2018 | Daon et al. |
| 2018/0071029 A1 | 3/2018 | Srimohanarajah et al. |
| 2018/0078316 A1 | 3/2018 | Schaewe et al. |
| 2018/0082480 A1 | 3/2018 | White et al. |
| 2018/0092667 A1 | 4/2018 | Heigl et al. |
| 2018/0092698 A1 | 4/2018 | Chopra et al. |
| 2018/0092699 A1 | 4/2018 | Finley |
| 2018/0116732 A1 | 5/2018 | Lin et al. |
| 2018/0116741 A1 | 5/2018 | Garcia et al. |
| 2018/0117150 A1 | 5/2018 | O'Dwyer |
| 2018/0120106 A1 | 5/2018 | Sato |
| 2018/0133871 A1 | 5/2018 | Farmer |
| 2018/0153626 A1 | 6/2018 | Yang et al. |
| 2018/0182150 A1 | 6/2018 | Benishti et al. |
| 2018/0185100 A1 | 7/2018 | Weinstein et al. |
| 2018/0185113 A1 | 7/2018 | Gregerson et al. |
| 2018/0193097 A1 | 7/2018 | McLachlin et al. |
| 2018/0200002 A1 | 7/2018 | Kostrzewski et al. |
| 2018/0247128 A1 | 8/2018 | Alvi et al. |
| 2018/0262743 A1 | 9/2018 | Casas |
| 2018/0303558 A1 | 10/2018 | Thomas |
| 2018/0311011 A1 | 11/2018 | Van Beek et al. |
| 2018/0317803 A1 | 11/2018 | Ben-Yishai et al. |
| 2018/0318035 A1 | 11/2018 | McLachlin et al. |
| 2018/0368898 A1 | 12/2018 | Divincenzo et al. |
| 2019/0000372 A1 | 1/2019 | Gullotti et al. |
| 2019/0000564 A1 | 1/2019 | Navab et al. |
| 2019/0015163 A1 | 1/2019 | Abhari et al. |
| 2019/0018235 A1 | 1/2019 | Ouderkirk et al. |
| 2019/0038362 A1 | 2/2019 | Nash et al. |
| 2019/0038365 A1 | 2/2019 | Soper |
| 2019/0043238 A1 | 2/2019 | Benishti et al. |
| 2019/0043392 A1 | 2/2019 | Abele |
| 2019/0046272 A1 | 2/2019 | Zoabi et al. |
| 2019/0046276 A1 | 2/2019 | Inglese et al. |
| 2019/0053851 A1 | 2/2019 | Siemionow et al. |
| 2019/0069971 A1 | 3/2019 | Tripathi et al. |
| 2019/0080515 A1 | 3/2019 | Geri et al. |
| 2019/0105116 A1 | 4/2019 | Johnson et al. |
| 2019/0130792 A1 | 5/2019 | Rios |
| 2019/0142519 A1 | 5/2019 | Siemionow et al. |
| 2019/0144443 A1 | 5/2019 | Jackson |
| 2019/0175228 A1 | 6/2019 | Elimelech et al. |
| 2019/0192230 A1 | 6/2019 | Siemionow et al. |
| 2019/0201106 A1 | 7/2019 | Siemionow et al. |
| 2019/0205606 A1 | 7/2019 | Zhou et al. |
| 2019/0216537 A1 | 7/2019 | Eltorai |
| 2019/0251692 A1 | 8/2019 | Schmidt-Richberg et al. |
| 2019/0251694 A1 | 8/2019 | Han et al. |
| 2019/0254753 A1 | 8/2019 | Johnson |
| 2019/0273916 A1 | 9/2019 | Benishti et al. |
| 2019/0310481 A1 | 10/2019 | Blum et al. |
| 2019/0333480 A1 | 10/2019 | Lang |
| 2019/0369660 A1 | 12/2019 | Wen et al. |
| 2019/0369717 A1 | 12/2019 | Frielinghaus |
| 2019/0378276 A1 | 12/2019 | Flossmann et al. |
| 2019/0387351 A1 | 12/2019 | Lyren |
| 2020/0019364 A1 | 1/2020 | Pond |
| 2020/0020249 A1 | 1/2020 | Jarc et al. |
| 2020/0038112 A1 | 2/2020 | Amanatullah |
| 2020/0043160 A1 | 2/2020 | Mizukura et al. |
| 2020/0078100 A1 | 3/2020 | Weinstein et al. |
| 2020/0085511 A1 | 3/2020 | Oezbek et al. |
| 2020/0088997 A1 | 3/2020 | Lee |
| 2020/0159313 A1 | 3/2020 | Gibby et al. |
| 2020/0100847 A1 | 4/2020 | Siegler et al. |
| 2020/0117025 A1 | 4/2020 | Sauer |
| 2020/0129058 A1 | 4/2020 | Li |
| 2020/0129136 A1 | 4/2020 | Harding et al. |
| 2020/0129262 A1 | 4/2020 | Verard |
| 2020/0129264 A1 | 4/2020 | Onativia et al. |
| 2020/0133029 A1 | 4/2020 | Yonezawa |
| 2020/0138518 A1 | 5/2020 | Lang |
| 2020/0138618 A1 | 5/2020 | Roszkowiak et al. |
| 2020/0143594 A1 | 5/2020 | Lal et al. |
| 2020/0146546 A1 | 5/2020 | Chene |
| 2020/0151507 A1 | 5/2020 | Siemionow et al. |
| 2020/0156259 A1 | 5/2020 | Morales |
| 2020/0163723 A1 | 5/2020 | Wolf et al. |
| 2020/0163739 A1 | 5/2020 | Messinger et al. |
| 2020/0184638 A1 | 6/2020 | Meglan |
| 2020/0186786 A1 | 6/2020 | Gibby et al. |
| 2020/0188028 A1 | 6/2020 | Feiner et al. |
| 2020/0188034 A1 | 6/2020 | Lequette et al. |
| 2020/0201082 A1 | 6/2020 | Carabin |
| 2020/0229877 A1 | 7/2020 | Siemionow et al. |
| 2020/0237256 A1 | 7/2020 | Farshad et al. |
| 2020/0237459 A1 | 7/2020 | Racheli et al. |
| 2020/0237880 A1 | 7/2020 | Kent |
| 2020/0242280 A1 | 7/2020 | Pavloff et al. |
| 2020/0246074 A1 | 8/2020 | Lang |
| 2020/0246081 A1 | 8/2020 | Johnson et al. |
| 2020/0264451 A1 | 8/2020 | Blum et al. |
| 2020/0265273 A1 | 8/2020 | Wei |
| 2020/0275988 A1 | 9/2020 | Johnson |
| 2020/0281554 A1 | 9/2020 | Trini et al. |
| 2020/0288075 A1 | 9/2020 | Bonin et al. |
| 2020/0294233 A1 | 9/2020 | Merlet |
| 2020/0297427 A1 | 9/2020 | Cameron et al. |
| 2020/0305980 A1 | 10/2020 | Lang |
| 2020/0315734 A1 | 10/2020 | El Amm |
| 2020/0321099 A1 | 10/2020 | Holladay et al. |
| 2020/0323460 A1 | 10/2020 | Busza |
| 2020/0323609 A1 | 10/2020 | Johnson et al. |
| 2020/0327721 A1 | 10/2020 | Siemionow et al. |
| 2020/0330179 A1 | 10/2020 | Ton |
| 2020/0337780 A1 | 10/2020 | Winkler |
| 2020/0341283 A1 | 10/2020 | McCracken |
| 2020/0352655 A1 | 11/2020 | Freese |
| 2020/0355927 A1 | 11/2020 | Marcellin-Dibon |
| 2020/0360091 A1 | 11/2020 | Murray et al. |
| 2020/0375666 A1 | 12/2020 | Murphy |
| 2020/0377493 A1 | 12/2020 | Heiser |
| 2020/0377956 A1 | 12/2020 | Vogelstein |
| 2020/0388075 A1 | 12/2020 | Kazanzides et al. |
| 2020/0389425 A1 | 12/2020 | Bhatia |
| 2020/0390502 A1 | 12/2020 | Holthuizen et al. |
| 2020/0390503 A1 | 12/2020 | Casas et al. |
| 2020/0402647 A1 | 12/2020 | Domracheva |
| 2020/0409306 A1 | 12/2020 | Gelman et al. |
| 2020/0410687 A1 | 12/2020 | Siemionow et al. |
| 2020/0413031 A1 | 12/2020 | Khani |
| 2021/0004956 A1 | 1/2021 | Book et al. |
| 2021/0009339 A1 | 1/2021 | Morrison et al. |
| 2021/0015560 A1 | 1/2021 | Boddington et al. |

(56) References Cited

U.S. PATENT DOCUMENTS

| | | |
|---|---|---|
| 2021/0015583 A1 | 1/2021 | Avisar |
| 2021/0022599 A1 | 1/2021 | Freeman et al. |
| 2021/0022808 A1 | 1/2021 | Lang |
| 2021/0022811 A1 | 1/2021 | Mahfouz |
| 2021/0022828 A1 | 1/2021 | Elimelech et al. |
| 2021/0029804 A1 | 1/2021 | Chang |
| 2021/0030374 A1 | 2/2021 | Takahashi |
| 2021/0030511 A1 | 2/2021 | Wolf et al. |
| 2021/0038339 A1 | 2/2021 | Yu |
| 2021/0049825 A1 | 2/2021 | Wheelwright et al. |
| 2021/0052348 A1 | 2/2021 | Schwagli et al. |
| 2021/0056687 A1 | 2/2021 | Hibbard et al. |
| 2021/0065911 A1 | 3/2021 | Goel et al. |
| 2021/0077195 A1 | 3/2021 | Saeidi |
| 2021/0077210 A1 | 3/2021 | Itkowitz |
| 2021/0080751 A1 | 3/2021 | Lindsey |
| 2021/0090344 A1 | 3/2021 | Geri et al. |
| 2021/0093391 A1 | 4/2021 | Poltaretskyi et al. |
| 2021/0093392 A1 | 4/2021 | Poltaretskyi et al. |
| 2021/0093400 A1 | 4/2021 | Quid et al. |
| 2021/0093417 A1 | 4/2021 | Liu |
| 2021/0104055 A1 | 4/2021 | Ni et al. |
| 2021/0107923 A1 | 4/2021 | Jackson |
| 2021/0109349 A1 | 4/2021 | Schneider |
| 2021/0109373 A1 | 4/2021 | Loo |
| 2021/0110517 A1 | 4/2021 | Flohr |
| 2021/0113269 A1 | 4/2021 | Vilsmeier |
| 2021/0113293 A9 | 4/2021 | Silva et al. |
| 2021/0121238 A1 | 4/2021 | Palushi et al. |
| 2021/0137634 A1 | 5/2021 | Lang et al. |
| 2021/0141887 A1 | 5/2021 | Kim et al. |
| 2021/0150702 A1 | 5/2021 | Claessen |
| 2021/0157544 A1 | 5/2021 | Denton |
| 2021/0160472 A1 | 5/2021 | Casas |
| 2021/0161614 A1 | 6/2021 | Elimelech et al. |
| 2021/0162287 A1 | 6/2021 | Xing |
| 2021/0165207 A1 | 6/2021 | Peyman |
| 2021/0169504 A1 | 6/2021 | Brown |
| 2021/0169578 A1 | 6/2021 | Calloway et al. |
| 2021/0169581 A1 | 6/2021 | Calloway et al. |
| 2021/0169605 A1 | 6/2021 | Calloway et al. |
| 2021/0186647 A1 | 6/2021 | Elimelech et al. |
| 2021/0196404 A1 | 7/2021 | Wang |
| 2021/0211640 A1 | 7/2021 | Bristol et al. |
| 2021/0223577 A1 | 7/2021 | Zheng |
| 2021/0225006 A1 | 7/2021 | Grady et al. |
| 2021/0227791 A1 | 7/2021 | De Oliveira Seixas |
| 2021/0231301 A1 | 7/2021 | Hikmet et al. |
| 2021/0235061 A1 | 7/2021 | Hegyi |
| 2021/0248822 A1 | 8/2021 | Choi |
| 2021/0278675 A1 | 9/2021 | Klug et al. |
| 2021/0282887 A1 | 9/2021 | Wiggermann |
| 2021/0290046 A1 | 9/2021 | Nazareth |
| 2021/0290336 A1 | 9/2021 | Wang |
| 2021/0290394 A1 | 9/2021 | Mahfouz |
| 2021/0295108 A1 | 9/2021 | Bar |
| 2021/0295512 A1 | 9/2021 | Knoplioch |
| 2021/0298795 A1 | 9/2021 | Bowling et al. |
| 2021/0298835 A1 | 9/2021 | Wang |
| 2021/0306599 A1 | 9/2021 | Pierce |
| 2021/0311322 A1 | 10/2021 | Belanger |
| 2021/0314502 A1 | 10/2021 | Liu |
| 2021/0315636 A1 | 10/2021 | Akbarian |
| 2021/0315662 A1 | 10/2021 | Freeman et al. |
| 2021/0325684 A1 | 10/2021 | Ninan |
| 2021/0333561 A1 | 10/2021 | Oh |
| 2021/0341739 A1 | 11/2021 | Cakmakci et al. |
| 2021/0341740 A1 | 11/2021 | Cakmakci et al. |
| 2021/0346115 A1 | 11/2021 | Dulin et al. |
| 2021/0349677 A1 | 11/2021 | Baldev |
| 2021/0364802 A1 | 11/2021 | Uchiyama et al. |
| 2021/0369226 A1 | 12/2021 | Siemionow et al. |
| 2021/0371413 A1 | 12/2021 | Thurston |
| 2021/0373333 A1 | 12/2021 | Moon |
| 2021/0373344 A1 | 12/2021 | Loyola |
| 2021/0378757 A1 | 12/2021 | Bay |
| 2021/0382310 A1 | 12/2021 | Freeman et al. |
| 2021/0386482 A1 | 12/2021 | Gera et al. |
| 2021/0389590 A1 | 12/2021 | Freeman |
| 2021/0400247 A1 | 12/2021 | Casas |
| 2021/0401533 A1 | 12/2021 | Im |
| 2021/0402255 A1 | 12/2021 | Fung |
| 2021/0405369 A1 | 12/2021 | King |
| 2022/0003992 A1 | 1/2022 | Ahn |
| 2022/0007006 A1 | 1/2022 | Healy et al. |
| 2022/0008135 A1 | 1/2022 | Frielinghaus et al. |
| 2022/0038675 A1 | 2/2022 | Hegyi |
| 2022/0039873 A1 | 2/2022 | Harris |
| 2022/0051484 A1 | 2/2022 | Jones et al. |
| 2022/0054199 A1 | 2/2022 | Sivaprakasam et al. |
| 2022/0061921 A1 | 3/2022 | Crawford et al. |
| 2022/0071712 A1 | 3/2022 | Wolf et al. |
| 2022/0079675 A1 | 3/2022 | Lang |
| 2022/0087746 A1 | 3/2022 | Lang |
| 2022/0113810 A1 | 4/2022 | Isaacs et al. |
| 2022/0117669 A1 | 4/2022 | Nikou et al. |
| 2022/0121041 A1 | 4/2022 | Hakim |
| 2022/0155861 A1 | 5/2022 | Myung |
| 2022/0159227 A1 | 5/2022 | Quiles Casas |
| 2022/0179209 A1 | 6/2022 | Cherukuri |
| 2022/0192776 A1 | 6/2022 | Gibby et al. |
| 2022/0193453 A1 | 6/2022 | Miyazaki et al. |
| 2022/0201274 A1 | 6/2022 | Achilefu et al. |
| 2022/0245400 A1 | 8/2022 | Siemionow et al. |
| 2022/0245821 A1 | 8/2022 | Ouzounis |
| 2022/0257206 A1 | 8/2022 | Hartley et al. |
| 2022/0269077 A1 | 8/2022 | Adema et al. |
| 2022/0270263 A1 | 8/2022 | Junio |
| 2022/0133484 A1 | 9/2022 | Lang |
| 2022/0287676 A1 | 9/2022 | Steines et al. |
| 2022/0295033 A1 | 9/2022 | Casas |
| 2022/0296315 A1 | 9/2022 | Sokhanvar et al. |
| 2022/0304768 A1 | 9/2022 | Elimelech et al. |
| 2022/0351385 A1 | 11/2022 | Finley et al. |
| 2022/0353487 A1 | 11/2022 | Hegyi |
| 2022/0358759 A1 | 11/2022 | Cork et al. |
| 2022/0370152 A1 | 11/2022 | Lavallee et al. |
| 2022/0387130 A1 | 12/2022 | Spaas et al. |
| 2022/0392085 A1 | 12/2022 | Finley et al. |
| 2022/0397750 A1 | 12/2022 | Zhou et al. |
| 2022/0398752 A1 | 12/2022 | Yoon et al. |
| 2022/0398755 A1 | 12/2022 | Herrmann |
| 2022/0405935 A1 | 12/2022 | Flossmann et al. |
| 2023/0004013 A1 | 1/2023 | McCracken et al. |
| 2023/0009793 A1 | 1/2023 | Gera et al. |
| 2023/0025480 A1 | 1/2023 | Kemp et al. |
| 2023/0027801 A1 | 1/2023 | Qian et al. |
| 2023/0032731 A1 | 2/2023 | Hrndler et al. |
| 2023/0034189 A1 | 2/2023 | Gera et al. |
| 2023/0050636 A1 | 2/2023 | Yanof et al. |
| 2023/0053120 A1 | 2/2023 | Jamali et al. |
| 2023/0073041 A1 | 3/2023 | Samadani et al. |
| 2023/0085387 A1 | 3/2023 | Jones et al. |
| 2023/0087783 A1 | 3/2023 | Dulin et al. |
| 2023/0100078 A1 | 3/2023 | Toporek et al. |
| 2023/0123621 A1 | 4/2023 | Joshi et al. |
| 2023/0126207 A1 | 4/2023 | Wang |
| 2023/0129056 A1 | 4/2023 | Hemingway et al. |
| 2023/0131515 A1 | 4/2023 | Oezbek et al. |
| 2023/0149083 A1 | 5/2023 | Lin et al. |
| 2023/0162493 A1 | 5/2023 | Worrell et al. |
| 2023/0165640 A1 | 6/2023 | Dulin et al. |
| 2023/0169659 A1 | 6/2023 | Chen et al. |
| 2023/0196582 A1 | 6/2023 | Grady et al. |
| 2023/0200917 A1 | 6/2023 | Calloway et al. |
| 2023/0236426 A1 | 7/2023 | Manly et al. |
| 2023/0236427 A1 | 7/2023 | Chen |
| 2023/0260142 A1 | 8/2023 | Chatterjee et al. |
| 2023/0290037 A1 | 9/2023 | Tasse et al. |
| 2023/0295302 A1 | 9/2023 | Bhagavatheeswaran et al. |
| 2023/0306590 A1 | 9/2023 | Jazdzyk et al. |
| 2023/0316550 A1 | 10/2023 | Hiasa |
| 2023/0326011 A1 | 10/2023 | Cutforth et al. |
| 2023/0326027 A1 | 10/2023 | Wahrenberg |

(56) References Cited

U.S. PATENT DOCUMENTS

| | | |
|---|---|---|
| 2023/0329799 A1 | 10/2023 | Gera et al. |
| 2023/0329801 A1 | 10/2023 | Elimelech et al. |
| 2023/0334664 A1 | 10/2023 | Lu et al. |
| 2023/0335261 A1 | 10/2023 | Reicher et al. |
| 2023/0359043 A1 | 11/2023 | Russell |
| 2023/0363832 A1 | 11/2023 | Mosadegh et al. |
| 2023/0371984 A1 | 11/2023 | Leuthardt et al. |
| 2023/0372053 A1 | 11/2023 | Elimelech et al. |
| 2023/0372054 A1 | 11/2023 | Elimelech et al. |
| 2023/0377171 A1 | 11/2023 | Hasler et al. |
| 2023/0377175 A1 | 11/2023 | Seok |
| 2023/0379448 A1 | 11/2023 | Benishti et al. |
| 2023/0379449 A1 | 11/2023 | Benishti et al. |
| 2023/0386022 A1 | 11/2023 | Tan et al. |
| 2023/0386067 A1 | 11/2023 | De et al. |
| 2023/0386153 A1 | 11/2023 | Rybnikov et al. |
| 2023/0394791 A1 | 12/2023 | Wang et al. |
| 2023/0397349 A1 | 12/2023 | Capelli et al. |
| 2023/0397957 A1 | 12/2023 | Crawford et al. |
| 2023/0410445 A1 | 12/2023 | Elimelech et al. |
| 2023/0419496 A1 | 12/2023 | Wuelker et al. |
| 2023/0420114 A1 | 12/2023 | Scholler et al. |
| 2024/0008935 A1 | 1/2024 | Wolf et al. |
| 2024/0016549 A1 | 1/2024 | Johnson et al. |
| 2024/0016572 A1 | 1/2024 | Elimelech et al. |
| 2024/0020831 A1 | 1/2024 | Johnson et al. |
| 2024/0020840 A1 | 1/2024 | Johnson et al. |
| 2024/0020862 A1 | 1/2024 | Johnson et al. |
| 2024/0022704 A1 | 1/2024 | Benishti et al. |
| 2024/0023946 A1 | 1/2024 | Wolf et al. |
| 2024/0041530 A1 | 2/2024 | Lang |
| 2024/0041558 A1 | 2/2024 | Siewerdsen et al. |
| 2024/0045491 A1 | 2/2024 | Sourov |
| 2024/0058064 A1 | 2/2024 | Weiser et al. |
| 2024/0062387 A1 | 2/2024 | Frantz et al. |
| 2024/0103271 A1 | 3/2024 | Zare Seisan |
| 2024/0103282 A1 | 3/2024 | Law et al. |
| 2024/0111163 A1 | 4/2024 | Law et al. |
| 2024/0122560 A1 | 4/2024 | Junio et al. |
| 2024/0126087 A1 | 4/2024 | Gera et al. |
| 2024/0127559 A1 | 4/2024 | Rybnikov et al. |
| 2024/0127578 A1 | 4/2024 | Hiasa |
| 2024/0129451 A1 | 4/2024 | Healy et al. |
| 2024/0130826 A1 | 4/2024 | Elimelech et al. |
| 2024/0134206 A1 | 4/2024 | Gera et al. |
| 2024/0144497 A1 | 5/2024 | Cvetko et al. |
| 2024/0156532 A1 | 5/2024 | Weiman et al. |
| 2024/0177445 A1 | 5/2024 | Galeotti et al. |
| 2024/0177458 A1 | 5/2024 | Zhang et al. |
| 2024/0180634 A1 | 6/2024 | Mikus |
| 2024/0184119 A1 | 6/2024 | Lee et al. |
| 2024/0185509 A1 | 6/2024 | Kovler et al. |
| 2024/0202926 A1 | 6/2024 | Crawford et al. |
| 2024/0202927 A1 | 6/2024 | Haslam et al. |
| 2024/0212111 A1 | 6/2024 | Genghi et al. |
| 2024/0233131 A1 | 7/2024 | Westerhoff et al. |
| 2024/0245463 A1 | 7/2024 | Vilsmeier et al. |
| 2024/0245474 A1 | 7/2024 | Weiman et al. |
| 2024/0248530 A1 | 7/2024 | Gibby et al. |
| 2024/0252252 A1 | 8/2024 | Lang |
| 2024/0261036 A1 | 8/2024 | Finley et al. |
| 2024/0261058 A1 | 8/2024 | Gera et al. |
| 2024/0265645 A1 | 8/2024 | Papar |
| 2024/0266033 A1 | 8/2024 | Freeman et al. |
| 2024/0268922 A1 | 8/2024 | Calloway et al. |
| 2024/0273740 A1 | 8/2024 | Gibby et al. |
| 2024/0281979 A1 | 8/2024 | Schrempf et al. |
| 2024/0296527 A1 | 9/2024 | Nett et al. |
| 2024/0303832 A1 | 9/2024 | Chen et al. |
| 2024/0307101 A1 | 9/2024 | Gera et al. |
| 2024/0312012 A1 | 9/2024 | Li et al. |
| 2024/0341861 A1 | 10/2024 | Wolf et al. |
| 2024/0341910 A1 | 10/2024 | Wolf et al. |
| 2024/0341911 A1 | 10/2024 | Elimelech et al. |

FOREIGN PATENT DOCUMENTS

| | | | |
|---|---|---|---|
| CN | 101379412 B | 3/2009 | |
| CN | 103106348 A | 5/2013 | |
| CN | 111915696 A | 11/2020 | |
| CN | 112489047 B | 3/2021 | |
| DE | 202004011567 U1 | 11/2004 | |
| DE | 102004011567 A1 | 9/2005 | |
| DE | 102014008153 A1 | 10/2014 | |
| DE | 202022103168 U1 | 6/2022 | |
| EP | 0933096 A2 | 8/1999 | |
| EP | 1640750 A1 | 3/2006 | |
| EP | 1757974 A1 | 2/2007 | |
| EP | 2119397 A1 | 11/2009 | |
| EP | 2557998 A1 | 2/2013 | |
| EP | 2823463 A1 | 1/2015 | |
| EP | 2868277 A1 | 5/2015 | |
| EP | 2134847 B1 | 6/2015 | |
| EP | 2963616 A2 | 1/2016 | |
| EP | 3028258 A1 | 6/2016 | |
| EP | 3037038 A1 | 6/2016 | |
| EP | 3069318 A1 | 9/2016 | |
| EP | 2891966 B1 | 1/2017 | |
| EP | 3121789 A1 | 1/2017 | |
| EP | 3123970 A1 | 2/2017 | |
| EP | 2654749 B1 | 5/2017 | |
| EP | 3175815 A1 | 6/2017 | |
| EP | 3216416 A1 | 9/2017 | |
| EP | 2032039 B1 | 10/2017 | |
| EP | 3247297 A1 | 11/2017 | |
| EP | 3256213 A1 | 12/2017 | |
| EP | 3306567 A1 | 4/2018 | |
| EP | 3320874 A1 * | 5/2018 | ............. A61B 10/02 |
| EP | 2030193 B1 | 7/2018 | |
| EP | 2225723 B1 | 2/2019 | |
| EP | 2619622 B1 | 2/2019 | |
| EP | 3034607 B1 | 3/2019 | |
| EP | 2892558 B1 | 4/2019 | |
| EP | 3494903 A1 | 6/2019 | |
| EP | 2635299 B1 | 7/2019 | |
| EP | 3505050 B1 | 7/2019 | |
| EP | 3224376 B1 | 8/2019 | |
| EP | 2875149 B1 | 12/2019 | |
| EP | 3206583 B1 | 9/2020 | |
| EP | 3711700 A1 | 9/2020 | |
| EP | 2625845 B1 | 3/2021 | |
| EP | 3076660 B1 | 4/2021 | |
| EP | 3858280 A1 | 8/2021 | |
| EP | 3593227 B1 | 9/2021 | |
| EP | 3913423 A1 | 11/2021 | |
| EP | 3789965 B1 | 12/2021 | |
| EP | 3634294 B1 | 1/2022 | |
| EP | 3952331 A1 | 2/2022 | |
| EP | 3960235 A1 | 3/2022 | |
| EP | 3635683 B1 | 7/2022 | |
| EP | 3602492 B1 | 11/2022 | |
| EP | 4173590 A1 | 5/2023 | |
| EP | 3533031 B1 | 8/2023 | |
| EP | 4252695 A1 | 10/2023 | |
| EP | 3195257 B1 | 11/2023 | |
| EP | 3405909 B1 | 11/2023 | |
| EP | 4270313 A1 | 11/2023 | |
| EP | 4287120 A1 | 12/2023 | |
| EP | 3488381 B1 | 2/2024 | |
| EP | 3834768 B1 | 2/2024 | |
| EP | 3903714 B1 | 2/2024 | |
| EP | 4336450 A1 | 3/2024 | |
| EP | 3814984 B1 | 4/2024 | |
| EP | 4115389 B1 | 4/2024 | |
| EP | 3752981 B1 | 5/2024 | |
| EP | 4375948 A1 | 5/2024 | |
| EP | 4383203 B1 | 6/2024 | |
| GB | 2507314 A | 4/2014 | |
| IL | 262864 A | 3/2019 | |
| JP | 2004-237092 A | 8/2004 | |
| JP | 2008-507361 A | 3/2008 | |
| JP | 2009-514571 A | 4/2009 | |
| JP | 2021-525186 A | 9/2021 | |
| KR | 20140120155 A | 10/2014 | |

(56) References Cited

FOREIGN PATENT DOCUMENTS

| | | |
|---|---|---|
| WO | 03034705 A2 | 4/2003 |
| WO | 2007051304 A1 | 5/2007 |
| WO | 2008103383 A1 | 8/2008 |
| WO | 2010067267 A1 | 6/2010 |
| WO | WO2010074747 A1 | 7/2010 |
| WO | WO2012101286 A1 | 8/2012 |
| WO | 2013112554 A1 | 8/2013 |
| WO | 2014024188 A1 | 2/2014 |
| WO | WO2014037953 A2 | 3/2014 |
| WO | 2014113455 A1 | 7/2014 |
| WO | 2014125789 A1 | 8/2014 |
| WO | 2014167563 A1 | 10/2014 |
| WO | 2014174067 A1 | 10/2014 |
| WO | 2015058816 A1 | 4/2015 |
| WO | WO2015061752 A1 | 4/2015 |
| WO | WO2015109145 A1 | 7/2015 |
| WO | WO-2016151506 A1 * 9/2016 ......... G02B 27/0172 |
| WO | WO2007115826 A2 | 10/2017 |
| WO | 2018/052966 A1 | 3/2018 |
| WO | 2018073452 A1 | 4/2018 |
| WO | WO2018200767 A1 | 4/2018 |
| WO | 2018206086 A1 | 11/2018 |
| WO | 2019/083431 A1 | 5/2019 |
| WO | 2019/135209 A1 | 7/2019 |
| WO | 2019/161477 A1 | 8/2019 |
| WO | 2019195926 A1 | 10/2019 |
| WO | 2019211741 A1 | 11/2019 |
| WO | WO2019210353 A1 | 11/2019 |
| WO | 2020109903 A1 | 6/2020 |
| WO | 2020109904 A1 | 6/2020 |
| WO | 2021019369 A1 | 2/2021 |
| WO | WO2021017019 A1 | 2/2021 |
| WO | WO2021023574 A1 | 2/2021 |
| WO | WO2021046455 A1 | 3/2021 |
| WO | WO2021048158 A1 | 3/2021 |
| WO | WO2021021979 A2 | 4/2021 |
| WO | WO2021061459 A1 | 4/2021 |
| WO | WO2021062375 A1 | 4/2021 |
| WO | WO2021073743 A1 | 4/2021 |
| WO | WO2021087439 A1 | 5/2021 |
| WO | WO2021091980 A1 | 5/2021 |
| WO | 2021255627 A1 | 6/2021 |
| WO | WO2021112918 A1 | 6/2021 |
| WO | 2021130564 A1 | 7/2021 |
| WO | WO2021137752 A1 | 7/2021 |
| WO | WO2021141887 A1 | 7/2021 |
| WO | WO2021145584 A1 | 7/2021 |
| WO | WO2021154076 A1 | 8/2021 |
| WO | 2021/188757 A1 | 9/2021 |
| WO | WO2021183318 A2 | 12/2021 |
| WO | WO2021257897 A1 | 12/2021 |
| WO | WO2021258078 A1 | 12/2021 |
| WO | WO2022009233 A1 | 1/2022 |
| WO | 2022053923 A1 | 3/2022 |
| WO | 2022079565 A1 | 4/2022 |
| WO | 2023/003952 A1 | 1/2023 |
| WO | 2023281395 A1 | 1/2023 |
| WO | 2023/011924 A1 | 2/2023 |
| WO | 2023007418 A1 | 2/2023 |
| WO | 2023021448 A1 | 2/2023 |
| WO | 2023021450 A1 | 2/2023 |
| WO | 2023021451 A1 | 2/2023 |
| WO | 2023/047355 A1 | 3/2023 |
| WO | 2023026229 A1 | 3/2023 |
| WO | 2023/072887 A1 | 5/2023 |
| WO | 2023/088986 A1 | 5/2023 |
| WO | 2023/158878 A1 | 8/2023 |
| WO | 2023/159104 A2 | 8/2023 |
| WO | 2023/161848 A1 | 8/2023 |
| WO | 2023/163933 A1 | 8/2023 |
| WO | 2023/175244 A1 | 9/2023 |
| WO | 2023/186996 A1 | 10/2023 |
| WO | 2023/202909 A1 | 10/2023 |
| WO | 2023/205212 A1 | 10/2023 |
| WO | 2023/205896 A1 | 11/2023 |
| WO | 2023/209014 A1 | 11/2023 |
| WO | 2023/229415 A1 | 11/2023 |
| WO | 2023/232492 A1 | 12/2023 |
| WO | 2023/240912 A1 | 12/2023 |
| WO | 2024/001140 A1 | 1/2024 |
| WO | 2024/002620 A1 | 1/2024 |
| WO | 2024/013642 A2 | 1/2024 |
| WO | 2024/018368 A2 | 1/2024 |
| WO | 2024/046760 A1 | 3/2024 |
| WO | 2024/052136 A1 | 3/2024 |
| WO | 2024/077077 A1 | 4/2024 |
| WO | 2024/121060 A1 | 6/2024 |
| WO | 2024/132609 A1 | 6/2024 |
| WO | 2024/145341 A1 | 7/2024 |
| WO | 2024/160896 A1 | 8/2024 |
| WO | 2024/165508 A1 | 8/2024 |
| WO | 2024/173251 A1 | 8/2024 |
| WO | 2024/186811 A1 | 9/2024 |

OTHER PUBLICATIONS

International Application # PCT/IB2020/056893 Search Report dated Nov. 9, 2020.

Mitrasinovic et al., "Clinical and surgical applications of smart glasses", pp. 381-401, Technology and Health Care, issue 23, year 2015.

Martin-Gonzalez et al., "Head-mounted virtual loupe with sight-based activation for surgical applications", IEEE symposium on mixed and augmented reality, pp. 207-208, Oct. 19-22, 2009.

Figl et al., "A fully automated calibration method for an optical see-through head-mounted operating microscope with variable zoom and focus", pp. 1492-1499, IEEE transactions on medical imaging, vol. 24, No. 11, Nov. 2005.

Medithinq Co. Ltd., "Metascope: world's first wearable scope", pp. 1-7, Jan. 2023.

Martin-Gonzalez et al., "Sight-based magnification system for surgical applications", pp. 26-30, Conference proceedings of Bildverarbeitung für die Medizin, year 2010.

Burstrom et al., "Frameless patient tracking with adhesive optical skin markers for augmented reality surgical navigation in spine surgery", Spine, vol. 45, No. 22, pp. 1598-1604, year 2020.

Suenaga et al., "Vision-based markerless registration using stereo vision and an augmented reality surgical navigation system: a pilot study", BMC Medical Imaging, pp. 1-11, year 2015.

Mayfield Clinic, "Spinal Fusion: Lateral Lumbar Interbody Fusion (LLIF)", pp. 1-6, Jan. 2021.

Qian et al., "AR-Loupe: Magnified Augmented Reality by Combining an Optical See-Through Head-Mounted Display and a Loupe", pp. 2550-2562, IEEE Transactions on Visualization and Computer Graphics, vol. 28, No. 7, Jul. 2022.

Kazanzides et al., "Systems and Methods for Augmented Reality Magnifying Loupe", case ID 15944, pp. 1-2, Nov. 26, 2020.

Liao et al., '3-D Augmented Reality for MRI-Guided Surgery Using Integral Videography Autostereoscopic Image Overlay', IEEE Transactions On Biomedical Engineering, vol. 57, No. 6, pp. 1476-1486, Feb. 17, 2010.

Hainich et al., "Near-Eye displays", Chapter 10 of Displays: Fundamentals and Applications, CRC press, pp. 439-504, Jul. 5, 2011.

Brainlab—Image Registration Options Enhanced Visualization Leveraging More Data , pp. 1-4, Feb. 2019.

Fingas., "Fraunhofer iPad app guides liver surgery through augmented reality", pp. 1-6, Aug. 22, 2013.

U.S. Appl. No. 16/419,023 Third party submission dated Jan. 19, 2020.

Sagitov et al., "Comparing Fiducial Marker Systems in the Presence of Occlusion", International Conference on Mechanical, System and Control Engineering (ICMSC), pp. 1-6, 2017.

Liu et al., "Marker orientation in fiducial registration", Medical Imaging 2003: Image Processing, Proceedings of SPIE vol. 5032, pp. 1176-1185, 2003.

U.S. Appl. No. 18/365,590, filed Aug. 4, 2023, Registration of a Fiducial Marker for an Augmented Reality System.

U.S. Appl. No. 18/365,571, filed Aug. 4, 2023, Registration of a Fiducial Marker for an Augmented Reality System.

(56) References Cited

OTHER PUBLICATIONS

U.S. Appl. No. 17/045,766, filed Oct. 7, 2020, Registration of a Fiducial Marker for an Augmented Reality System.
U.S. Appl. No. 16/524,258, filed Jul. 29, 2019, Fiducial Marker.
U.S. Appl. No. 16/200,144, now U.S. Pat. No. 11,766,296, Nov. 26, 2018, Sep. 26, 2023, Tracking Methods for Image-Guided Surgery.
U.S. Appl. No. 18/470,809, filed Sep. 20, 2023, Tracking Methods for Image-Guided Surgery.
U.S. Appl. No. 18/437,898, filed Feb. 9, 2024, Iliac Pin and Adapter.
U.S. Appl. No. 18/576,516, filed Jan. 4, 2024, Iliac Pin and Adapter.
U.S. Appl. No. 17/388,064, filed Jul. 29, 2021, Rotating Marker and Adapter for Image-Guided Surgery.
U.S. Appl. No. 18/291,731, filed Jan. 24, 2024, Rotating Marker and Adapter for Image-Guided Surgery.
U.S. Appl. No. 18/365,844, filed Aug. 4, 2023, Augmented-Reality Surgical System Using Depth Sensing.
U.S. Appl. No. 18/683,676, filed Feb. 14, 2024, Stereoscopic Display and Digital Loupe for Augmented-Reality Near-Eye Display.
U.S. Appl. No. 18/683,680, filed Feb. 14, 2024, Augmented Reality Assistance for Osteotomy and Discectomy.
U.S. Appl. No. 18/684,756, filed Feb. 19, 2024, Registration and Registration Validation in Image-Guided Surgery.
U.S. Appl. No. 18/365,566, filed Aug. 4, 2023, Systems for Medical Image Visualization.
U.S. Appl. No. 18/399,253, filed Dec. 28, 2023, Methods for Medical Image Visualization.
U.S. Appl. No. 18/398,837, filed Dec. 28, 2023, Adjustable Augmented Reality Eyewear for Image-Guided Medical Intervention.
U.S. Appl. No. 18/399,433, filed Feb. 28, 2023, Configurable Augmented Reality Eyewear for Image-Guided Medical Intervention.
International Application PCT/IB2022/057965 Search Report dated Dec. 15, 2022.
U.S. Appl. No. 16/524,258 Office Action dated Jan. 24, 2023.
International Application PCT/IB2022/057733 Search Report dated Jan. 26, 2023.
European Application 22203956.2 Search Report dated Feb. 9, 2023.
International Application PCT/IB2022/059030 Search report dated Feb. 28, 2023.
CN Application # 2019800757525 Office Action dated Mar. 1, 2022.
U.S. Appl. No. 16/200,144 Office Action dated Mar. 15, 2022.
U.S. Appl. No. 16/524,258 Office Action dated Apr. 11, 2022.
EP Application # 16767845.7 Office Action dated Apr. 29, 2022.
U.S. Appl. No. 16/419,023 Office Action dated Mar. 1, 2022.
Lorensen et al., "Marching Cubes: A High Resolution 3D Surface Construction Algorithm," ACM SIGGRAPH '87, Computer Graphics, vol. 21, No. 4, pp. 163-169, Jul. 1987.
Wikipedia, "Marching Cubes," pp. 1-4, last edited Sep. 4, 2021.
Milletari et al., "V-Net: fully Convolutional Neural Networks for Volumetric Medical Image Segmentation," arXiv:1606.04797v1, pp. 1-11, Jun. 15, 2016.
Webster (ed.), "Structured Light Techniques and Applications," Wiley Encyclopedia of Electrical and Electronics Engineering, pp. 1-24, year 2016.
Liberadzki et al., "Structured-Light-Based System for Shape Measurement of the Human Body in Motion," Sensors, vol. 18, pp. 1-19, year 2018.
Romero, "vol. Ray Casting Techniques and Applications Using General Purpose Computations on Graphics Processing Units," Thesis/Dissertation Collections, Rochester Institute of Technology, RIT Scholar Works, pp. 1-140, Jun. 2009.
Zhang et al., "Medical Volume Rendering Techniques," Independent Research, Spring 2014, arXiv:1802.07710v1, pp. 1-33, Feb. 21, 2018.
Van Ooijen et al., "Noninvasive Coronary Imaging Using Electron Beam CT: Surface Rendering Versus Volume Rendering," Computers in Radiology, AJR, vol. 180, pp. 223-226, Jan. 2003.
Lumus Ltd., "DK-32 See-through Wearable Display Development Kit," Rehovot, Israel, pp. 1-2, Dec. 24, 2013.
Messinger et al., U.S. Appl. No. 16/231,656, filed Dec. 24, 2018.
EP Application # 19891059.8 Search Report dated Jul. 27, 2022.
EP Application # 19890849.3 Search Report dated Jul. 27, 2022.
U.S. Appl. No. 16/419,023 Office Action dated Sep. 1, 2022.
U.S. Appl. No. 16/524,258 Office Action dated Oct. 24, 2022.
International Application PCT/IB2022/059030 filed Sep. 23, 2022.
JP Application # 2021525186 Office Action dated Dec. 1, 2021.
EP Application # 19796580.9 Search Report dated Dec. 20, 2021.
International Application # PCT/IB2021/058088 Search Report Dec. 20, 2021.
Gera et al., U.S. Appl. No. 17/388,064, filed Jul. 29, 2021.
Gera et al., U.S. Appl. No. 16/901,026, filed Jun. 15, 2020.
Wolf et al., U.S. Appl. No. 17/015,199, filed Sep. 9, 2020.
Elimelech et al., U.S. Appl. No. 17/045,766, filed Oct. 7, 2020.
U.S. Appl. No. 15/896,102, now U.S. Pat. No. 10,134,166, Feb. 14, 2018, (Nov. 20, 2018), Combining Video-Based and Optic-Based Augmented Reality in a Near Eye Display.
U.S. Appl. No. 16/159,740, now U.S. Pat. No. 10,382,748, Oct. 15, 2018 (Aug. 13, 2019), Combining Video-Based and Optic-Based Augmented Reality in a Near Eye Display.
U.S. Appl. No. 16/419,023, now U.S. Pat. No. 11,750,794, May 22, 2019, (Sep. 5, 2023), Combining Video-Based and Optic-Based Augmented Reality in a Near Eye Display.
U.S. Appl. No. 18/352,158, filed Jul. 13, 2023, Combining Video-Based and Optic-Based Augmented Reality in a Near Eye Display.
U.S. Appl. No. 18/365,643, filed Aug. 4, 2023, Head-Mounted Augmented Reality Near Eye Display Device.
U.S. Appl. No. 18/365,650, filed Aug. 4, 2023, Systems for Facilitating Augmented Reality-Assisted Medical Procedures.
U.S. Appl. No. 15/127,423, now U.S. Pat. No. 9,928,629, Sep. 20, 2016, (Mar. 27, 2018), Combining Video-Based and Optic-Based Augmented Reality in a Near Eye Display.
U.S. Appl. No. 16/120,480, now U.S. Pat. No. 10,835,296, Sep. 4, 2018, (Nov. 17, 2020), Spinous Process Clamp.
U.S. Appl. No. 17/067,831, filed Oct. 12, 2020, Spinous Process Clamp.
U.S. Appl. No. 18/030,072, filed Apr. 4, 2023, Spinous Process Clamp.
U.S. Appl. No. 18/365,590, now U.S. Pat. No. 11,980,508, Aug. 4, 2023, (May 14, 2024), Registration of a Fiducial Marker for an Augmented Reality System.
U.S. Appl. No. 18/365,571, now U.S. Pat. No. 11,974,887, Aug. 4, 2023, (May 7, 2024), Registration Marker for an Augmented Reality System.
U.S. Appl. No. 18/632,588, filed Apr. 11, 2024, Registration of a Fiducial Marker for an Augmented Reality System.
U.S. Appl. No. 17/045,766, now U.S. Pat. No. 11,980,507, Oct. 7, 2020, (May 14, 2024), Registration of a Fiducial Marker for an Augmented Reality System.
U.S. Appl. No. 16/199,281, now U.S. Pat. No. 10,939,977, Nov. 26, 2018, (Mar. 9, 2021), Positioning Marker.
U.S. Appl. No. 16/524,258, now U.S. Pat. No. 11,980,506, Jul. 29, 2019, (May 14, 2024), Fiducial Marker.
U.S. Appl. No. 18/631,804, filed Apr. 10, 2024, Fiducial Marker.
U.S. Appl. No. 17/585,629, filed Jan. 27, 2022, Fiducial Marker.
U.S. Appl. No. 16/724,297, now U.S. Pat. No. 11,382,712, Dec. 22, 2019, (Jul. 12, 2022), Mirroring in Image Guided Surgery.
U.S. Appl. No. 17/827,710, now U.S. Pat. No. 11,801,115, May 29, 2022, (Oct. 31, 2023), Mirroring in Image Guided Surgery.
U.S. Appl. No. 18/352,181, filed Jul. 13, 2023, Mirroring in Image Guided Surgery.
U.S. Appl. No. 18/400,739, filed Dec. 29, 2023, Mirroring in Image Guided Surgery.
U.S. Appl. No. 16/200,144, now U.S. Pat. No. 11,766,296, Nov. 26, 2018, (Sep. 26, 2023), Tracking Systems and Methods for Image-Guided Surgery.
U.S. Appl. No. 18/470,809 now U.S. Pat. No. 11,980,429, Sep. 20, 2023 (May 14, 2024), Tracking Systems and Methods for Image-Guided Surgery.
U.S. Appl. No. 18/631,877, filed Apr. 10, 2024, Tracking Systems and Methods for Image-Guided Surgery.

(56) References Cited

OTHER PUBLICATIONS

U.S. Appl. No. 17/015,199, filed Sep. 9, 2020, Universal Tool Adapter.
U.S. Appl. No. 18/598,965, filed Mar. 7, 2024, Universal Tool Adapter for Image Guided Surgery.
U.S. Appl. No. 18/044,380, filed Mar. 8, 2023, Universal Tool Adapter for Image-Guided Surgery.
U.S. Appl. No. 16/901,026, now U.S. Pat. No. 11,389,252, Jun. 15, 2020, (Jul. 19, 2022), Rotating Marker for Image Guided Surgery.
U.S. Appl. No. 18/008,980, filed Dec. 8, 2022, Rotating Marker.
U.S. Appl. No. 17/368,859, now U.S. Pat. No. 11,896,445, Jul. 7, 2021, (Feb. 13, 2024), Iliac Pin and Adapter.
U.S. Appl. No. 18/,437,898, Feb. 9, 2024, Iliac Pin and Adapter.
U.S. Appl. No. 18/576,516, Jan. 4, 2024, Iliac Pin and Adapter.
U.S. Appl. No. 17/388,064, Jul. 29, 2021, Rotating Marker and Adapter for Image-Guided Surgery.
U.S. Appl. No. 18/291,731, Jan. 24, 2024, Rotating Marker and Adapter for Image-Guided Surgery.
U.S. Appl. No. 18/365,844, Aug. 4, 2023, Augmented-Reality Surgical System Using Depth Sensing.
U.S. Appl. No. 18/683,676, Feb. 14, 2024, Stereoscopic Display and Digital Loupe for Augmented-Reality Near-Eye Display.
U.S. Appl. No. 18/683,680, Feb. 14, 2024, Augmented Reality Assistance for Osteotomy and Discectomy.
U.S. Appl. No. 18/684,756, Feb. 19, 2024, Registration and Registration Validation in Image-Guided Surgery.
U.S. Appl. No. 18/693,338, Mar. 19, 2024, Surgical Planning and Display.
U.S. Appl. No. 18/365,566, Aug. 4, 2023, Systems for Medical Image Visualization.
U.S. Appl. No. 18/399,253, Dec. 28, 2023, Methods for Medical Image Visualization.
U.S. Appl. No. 18/398,837, now U.S. Pat. No. 12,044,858, Dec. 28, 2023, (Jul. 23, 2024), Adjustable Augmented Reality Eyewear for Image-Guided Medical Intervention.
U.S. Appl. No. 18/399,433, now U.S. Pat. No. 12,044,856, Dec. 28, 2023, (Jul. 23, 2024), Configurable Augmented Reality Eyewear for Image-Guided Medical Intervention.
U.S. Appl. No. 35/508,942, now U.S. Pat. No. D. 930,162, Feb. 13, 2020, (Sep. 7, 2021), Medical Headset.
16 Augmented Reality Glasses of 2021 (with Features), in Back to News, Dated May 6, 2022, accessed at https://web.archive.org/web/20221127195438/https://circuitstream.com/blog/16-augmented-reality-glasses-of-2021-with-features-breakdowns/.
Everysight, Installing your RX Adaptor, accessed Mar. 13, 2024 at https://support.everysight.com/hc/en-us/articles/115000984571-Installing-your-RX-Adaptor.
Everysight, Raptor User Manual, copyright 2017, in 46 pages.
Frames Direct, InSpatialRx Prescription Insert, Prescription Insert for Magic Leap 1, accessed Mar. 8, 2024 at https://www.framesdirect.com/inspatialrx-prescription-insert.html.
Reddit, Notice on Prescription Lenses for Nreal Glasses, accessed Mar. 13, 2024 at https://www.reddit.com/r/nreal/comments/x1fte5/notice_on_prescription_lenses_for_nreal_glasses/.
Vuzix Blades, Prescription Lens Installation Guide, copyright 2020.

\* cited by examiner

FIDUCIAL MARKER

CROSS-REFERENCE TO RELATED APPLICATIONS

This application is a continuation in part of PCT Patent Application PCT/IB2020/056893, filed Jul. 22, 2020, which is a continuation in part of U.S. patent application Ser. No. 16/524,258 now U.S. Pat. No. 11,980,506, filed Jul. 29, 2019.

FIELD OF THE INVENTION

The present invention relates generally to a fiducial marker, and specifically to a marker that can be used for registration of multiple frames of reference present in image guided surgery.

BACKGROUND OF THE INVENTION

In an augmented reality system that is used for image guided surgery the system should track objects used in the surgery, and/or elements of the patient undergoing the surgery. The tracking requires registration of different frames of reference operative during the surgery, including a frame of reference of the patient and a frame of reference of a fluoroscopy facility imaging the patient. The registration typically requires a fiducial marker, and a number of such markers are known. References describing examples of markers are given below.

U.S. Pat. No. 6,314,310 to Ben-Haim et al. describes apparatus for X-ray guided surgery. The apparatus includes a reference element which is placed in contact with the body of a subject, and the element includes a plurality of fiducial marks.

U.S. Pat. No. 7,107,091 to Jutras et al. describes a surgical device that is adapted for use with an image guided surgical system. The device facilitates monitoring inter-dependently mobile bone elements.

U.S. Pat. No. 9,179,984 to Teichman et al. describes a navigation system that includes a multi-configuration tracking array. A plurality of tracking devices can be positioned on the multi-configuration tracking array.

U.S. Pat. No. 9,498,231 to Haider et al. describes computer aided surgery utilizing an on tool tracking system.

U.S. Pat. No. 9,844,413 to Doan et al. describes a monitoring system that tracks the non-visible structure of a body in three dimensions. A tracker obtains image information of an object and instruments in its vicinity, all bearing 3D tracking markers with at least one pattern segment.

U.S. Pat. No. 9,872,733 to Shoham et al. describes a system providing a mechanical guide for drilling the holes for distal screws in intramedullary nailing surgery. The drill guide is automatically positioned by a robot relative to the distal locking nail holes, using data derived from X-ray fluoroscopic images.

U.S. Pat. No. 10,034,713 and U.S. Patent Application 2017/0252109 to Yang et al. describe a system for tracking a position and orientation of a handheld implement. A support member secures one or more markers relative to a longitudinal portion of the handheld implement, and a marker plane containing the markers is orientated at an angle relative to a longitudinal axis of the longitudinal portion.

U.S. Pat. No. 10,080,616 to Wilkinson et al. describes a system that accesses image data of a bone to which a reference marker array is fixed.

U.S. Pat. No. 10,085,709 and U.S. Patent Application 2017/0164919 to Lavallee et al. describe projecting a 3D image on at least part of 2D X-ray images and adjusting projective geometry data of the images, the adjustment comprising registration of the images with the projection of an initial 3D image using an image-to-image registration technique.

U.S. Pat. No. 10,166,079 to McLachlin et al. describes performing intraoperative image registration during a medical procedure. A depth-encoded marker is provided to an object of interest. The marker is imageable by at least two imaging systems, and the marker has asymmetry in at least a depth dimension.

U.S. Pat. No. 10,194,993 to Roger et al. describes a system for aiding surgery on a patient. The system includes a display device and a storage device that stores an image of at least a portion of the anatomy of the patient, including one or more surgical navigation markers positioned on the patient, for display on the display device.

U.S. Patent Application 2011/0004259 to Stallings et al. describes a device for positioning a fiducial marker on an anatomical structure. The device includes a fiducial base and a fixation member. The fiducial base comprises a turn and an extension configured to position the fiducial marker within the field of view of a tracking sensor.

U.S. Patent Application 2011/0098553 to Robbins et al. describes automatic registration of a magnetic resonance (MR) image is carried out in an image guidance system by placing MR visible markers at known positions relative to markers visible in a camera tracking system.

U.S. Patent Application 2015/0150641 to Doan et al. describes a position and orientation tracking system having one or more pattern tags, each tag comprising a plurality of contrasting portions. There is a tracker for obtaining image information about the pattern tags, and a database with geometric information describing patterns on the pattern tags.

U.S. Patent Application 2015/0366620 to Cameron et al. describes a guide for use with an access port for port-based surgery. The guide includes a body positionable over a surgical opening and a grip coupled to the body for removably receiving the access port into the surgical opening.

U.S. Patent Application 2017/0281283 to Siegler et al. describes tracking marker support structures that include one or more fiducial reference markers, where the tracking marker support structures are configured to be removably and securely attached to a skeletal region of a patient.

U.S. Patent Application 2018/0200002 to Kostrzewski describes robotic surgical systems with built-in navigation capability for patient position tracking and surgical instrument guidance during a surgical procedure, without the need for a separate navigation system.

U.S. Patent Application 2018/0318035 to McLachlin et al. describes a reference tie that is to be secured around a portion of a spine during a surgical procedure and that is to be tracked by a surgical navigation system.

U.S. Patent Application 2019/0015163 to Abhari et al. describes how navigational information relative to a site of a medical procedure is determined. The navigational information is then mapped to a common coordinate space, to determine the navigational information relative to a field of view of saved and live optical images of the surgical site.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a medical marking device, including:
a radiotransparent plate having a first plurality of radiopaque elements embedded therein in a first predefined pattern and a second plurality of optical reflectors positioned on a surface in proximity to the plate in a second predefined pattern; and
a sigmoid mounting arm having a first end connected to the radiotransparent plate and a second end containing one or more fastening receptacles.

Typically, the sigmoid mounting arm is radiotransparent.

In a disclosed embodiment the sigmoid mounting arm consists of a first curved section connected to a second curved section by a straight section.

In a further disclosed embodiment the sigmoid mounting arm consists of a first curved section connected directly to a second curved section.

In a yet further disclosed embodiment the first and the second predefined patterns have no axes of symmetry and no planes of symmetry.

There is further provided, according to an embodiment of the present invention, apparatus, including:
a surgical clamp for attachment to a bone of a patient;
a spacer having a first surface and a second surface configured to connect fixedly to the surgical clamp; and
a marking device, which includes:
a radiotransparent plate having a plurality of radiopaque elements embedded therein in a predefined pattern; and
a sigmoid mounting arm having a first end fixedly connected to the radiotransparent plate and a second end, configured to mate with the first surface of the spacer, and containing one or more fastening receptacles configured for removable connection of the arm from the spacer.

In an alternative embodiment there is a fixed distance between the first and spacer surfaces.

In a further alternative embodiment the first surface includes a first plate and the second surface includes a second plate, the apparatus further having an adjustable mechanism connecting the first and the second plate configured to adjust a separation of the plates.

There is further provided, according to an embodiment of the invention, apparatus, including:
a surgical clamp for attachment to a bone of a patient;
clamp adjustment elements configured to effectuate the attachment;
a support structure enclosing the clamp adjustment elements; and
a marking device, which consists of:
a radiotransparent plate having a plurality of radiopaque elements embedded therein in a predefined pattern; and
a sigmoid mounting arm having a first end fixedly connected to the radiotransparent plate and a second end containing one or more fastening receptacles configured for removable connection of the arm from the support structure.

There is further provided, according to an embodiment of the invention, a method, including:
embedding a first plurality of radiopaque elements, arranged in a first predefined pattern, in a radiotransparent plate;
positioning a second plurality of optical reflectors on a surface in proximity to the plate in a second predefined pattern; and
connecting a first end of a sigmoid mounting arm to the radiotransparent plate, the arm having a second end containing one or more fastening receptacles.

There is further provided, according to an embodiment of the invention, a method, including:
attaching a surgical clamp to a bone of a patient;
embedding a first plurality of radiopaque elements, arranged in a first predefined pattern, in a radiotransparent plate and positioning a second plurality of optical reflectors on a surface in proximity to the plate in a second predefined pattern;
connecting a first end of a sigmoid mounting arm to the surgical clamp, the arm having a second end fixedly connected to the radiotransparent plate;
fluoroscopically scanning the radiotransparent plate, the sigmoid mounting arm, and the surgical clamp so as to form a fluoroscopic scan;
optically scanning the second plurality of optical reflectors so as to form a first optical scan;
disconnecting the first end of the sigmoid mounting arm from the surgical clamp and connecting a patient marker, having a third plurality of reflectors in a third predefined pattern, to the surgical clamp;
optically scanning the third plurality of optical reflectors so as to form a second optical scan;
deriving from the first and the second optical scans a correction vector indicative of a difference between a location and an orientation of the radiotransparent plate and a location and an orientation of the patient marker; and
in response to the correction vector and the fluoroscopic scan, determining a spatial transformation between the patient and the surgical clamp so as register a frame of reference of the patient with a frame of reference of the surgical clamp.

Typically, the method includes, in response to registration of the frames of reference, presenting to a professional performing surgery on the patient a stored image of the patient aligned with the patient.

The present disclosure will be more fully understood from the following detailed description of the embodiments thereof, taken together with the drawings, in which:

DETAILED DESCRIPTION OF EMBODIMENTS

Overview

Figure 1:
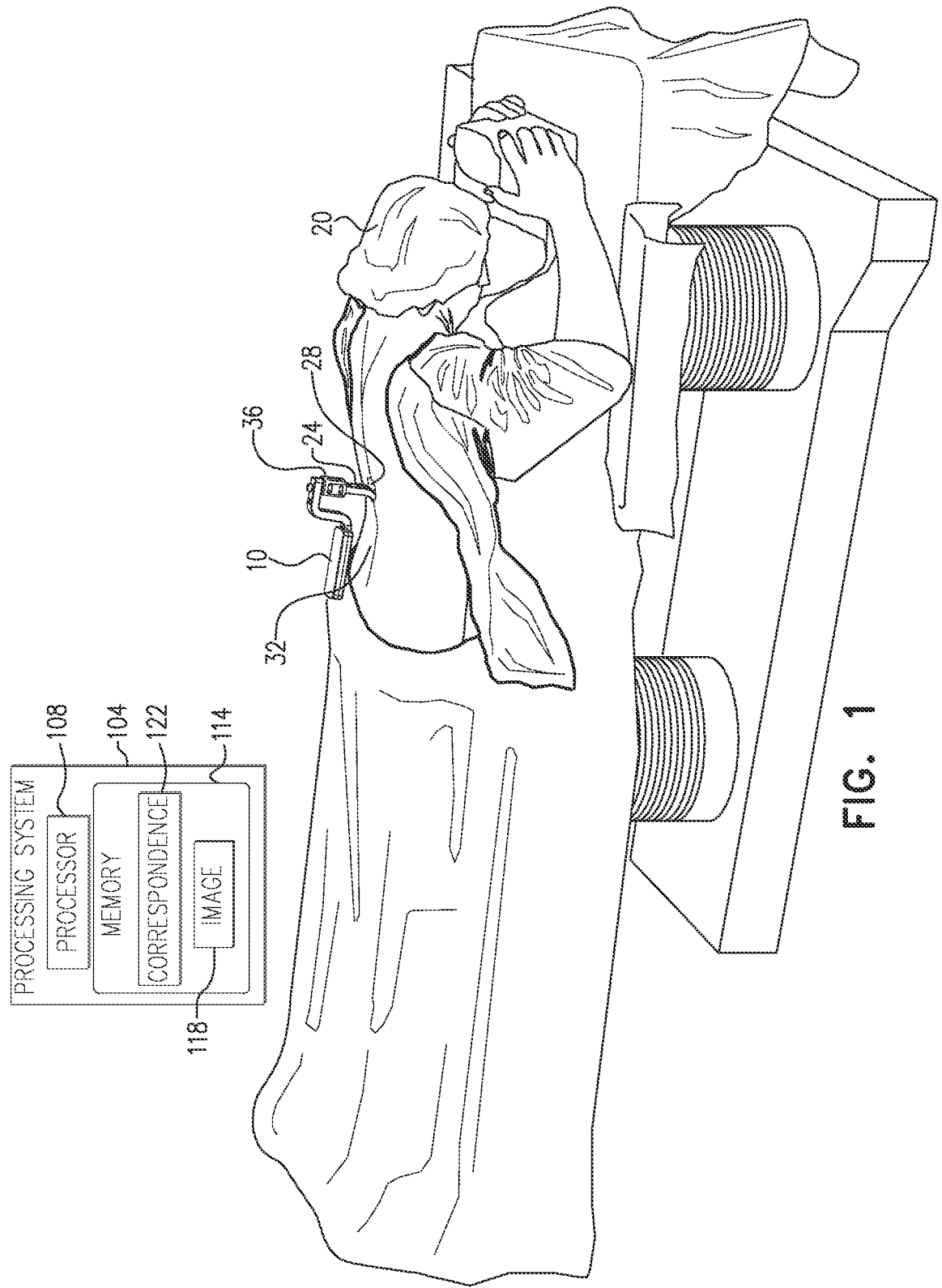
FIG. 1 is a schematic diagram illustrating a medical marking device as it is used during a preparatory stage of a medical procedure, according to an embodiment of the present invention.

An embodiment of the present invention provides a fiducial marker that is used to register different frames of reference that are present in image guided surgery on a patient. The image guided surgery may be performed by a medical professional wearing an augmented reality head-mounted display, and in order for the display to operate correctly, images of the patient presented to the professional should align with the actual patient. The registration provided by the fiducial marker ensures the necessary image alignment.

In a disclosed embodiment the marker is connected to a clamp which has been attached, in a preparatory stage of a procedure performed on a patient, to one or more spinous processes of the patient. To accommodate physical differences between patients, embodiments of the invention provide alternative systems for attaching the fiducial marker to the clamp, the alternative systems including fixed width and variable width spacers connecting the marker to the clamp.

The fiducial marker comprises radiopaque elements arranged in a predetermined pattern, so that a computerized tomography (CT) scanned image of the marker and of the patient enables frames of reference of the patient's anatomy and of the clamp to be registered in the preparatory stage.

In a subsequent stage of the procedure the fiducial marker is replaced by a patient marker. In some embodiments of the invention the fiducial marker also comprises optical reflectors and images of these may be used to accommodate different positions of the patient marker.

The registration derived in the preparatory stage is used in the subsequent stage of the procedure so that images of the patient marker are used to track the patient, and to ensure that images presented to the professional are correctly aligned.

The CT facility typically comprises an intraoperative CT scanner which has a narrow field of view, so that for the registration to be successful, the radiopaque elements of the fiducial marker and the vertebral bodies should be close. Embodiments of the invention achieve this close proximity by having the fiducial marker in the form of a "step," with one part of the step comprising a plate containing the radiopaque elements, the step-like form of the fiducial marker enabling the plate to be positioned close to the vertebral bodies. A second part of the step attaches to the clamp, and there is a known mechanical offset between the two parts.

In embodiments of the present invention the plate is radiotransparent, and has the plurality of radiopaque elements referred to above embedded therein in the predetermined pattern. To achieve the step-like form described above, a first end of a sigmoid mounting arm is fixedly connected to the radiotransparent plate. In addition, the sigmoid mounting arm has a second end containing one or more fastening receptacles that are configured for removable connection of the arm to the clamp that is attached to the spinous processes.

In a disclosed embodiment the radiotransparent plate, the sigmoid mounting arm, and the surgical clamp are scanned fluoroscopically so as to form a fluoroscopic scan. In response to the fluoroscopic scan and the predetermined mechanical offset, a spatial transformation between the patient and the surgical clamp is determined so as to register a frame of reference of the patient with a frame of reference of the surgical clamp.

Typically, in response to registration of the frames of reference, a professional performing surgery on the patient is presented with a stored image of the patient aligned with the patient.

While the description herein refers to a fiducial marker or a patient marker being connected to a clamp that is attached to one or more spinous processes of vertebrae of a patient, it will be understood that the scope of the invention comprises any marker retaining structure, not just a clamp, that is rigidly attached to any bone of the patient. For example, the retaining structure may comprise an iliac pin that is rigidly inserted into an ilium of the patient. As is the case for the clamp, a fiducial marker or a patient marker may be connected to the retaining structure.

The different frames of reference referred to above comprise a patient frame of reference, a clamp frame of reference, a fiducial marker frame of reference, and a patient marker frame of reference. As is described herein, during the course of a procedure on the patient, the different frames of reference are registered with each other, so that during the image guided surgery images presented to the professional wearing the head mounted display align with the patient.

The registration between any two of the different frames of reference may be by imaging the two associated different elements in a single image, and calculating the registration between the frames of reference from the imaged elements in the single image. For example, the fiducial marker frame of reference may be registered with the patient frame of reference by acquiring then analyzing a fluoroscopic image of the fiducial marker and of a bone of the patient, after the fiducial marker has been rigidly attached to the bone. Alternatively, in the case that the clamp is visible in the fluoroscopic image, both the fiducial marker frame of reference and the clamp frame of reference may be registered with the patient frame of reference by analysis of the image.

Alternatively or additionally, the registration between any two frames of reference may be accomplished if the physical dimensions of the two associated different elements, and how the elements are physically connected together, are known or may be determined. For example, as is described in more detail below, the dimensions of the patient marker and the clamp, and how the patient marker is connected to the clamp, are known. From the known dimensions and method of connection, the frames of reference of the patient marker may be registered with the clamp.

Since the clamp is rigidly attached to the patient, the registrations between the frames of reference of the patient marker and the clamp, and between the frames of reference of the clamp and the patient are transitive relations, Consequently the two registrations may be combined, as is described below, to form a direct registration between the frames of reference of the patient marker and the patient.

In cases where an image of the clamp is not available, it will be understood that such a direct registration may be formed, without using an image of the clamp as an intermediary, if the dimensions of the patient marker and the clamp, and their physical and method of connection, are known, and if the dimensions and physical method of connection of the clamp to the patient are known. In this case dimensions directly relating the patient marker to the patient are known, and these may be used to calculate the registration between the two entities.

System Description

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Reference is now made to FIG. 1, which is a schematic diagram illustrating a medical marking device 10, as it is used during a preparatory stage of a medical procedure on a patient 20, according to an embodiment of the present invention. The procedure referred to herein is assumed to comprise a preparatory stage and a subsequent stage, and, as is described in more detail below, device 10 may be used during the preparatory stage. Device 10 is also herein termed a fiducial marker 10. As is also described below, a medical professional uses an augmented reality system during the subsequent stage of the procedure.

The augmented reality system projects virtual images of elements of patient 20 for viewing by the medical professional. The image projection is performed simultaneously with the professional viewing the actual patient, so that the projected images should align with the patient. In order for the projected images in the augmented reality system to align with the patient, frames of reference of the patient and of a clamp attached to a bone of the patient are registered during the preparatory stage, using marking device 10. In the subsequent stage, where the augmented reality system is used, the registration of the clamp computed in the preparatory phase is used to correctly align the images produced by the system.

In the description herein the procedure is assumed to comprise an operation on a spine of patient 20, and in order to perform the registration referred to above, prior to the operation, and in the preparatory stage of the procedure, the medical professional inserts a surgical bone clamp 24 into patient 20. A site of insertion 28 of the clamp is close to, but separate from, a site 32 of the patient's spine to be operated on during the subsequent stage of the procedure. The professional clamps clamp 24 to a section of the spine of the patient, typically to one or more spinous processes of the patient, and the clamp has a support structure 36 to which marker 10 is fastened. A clamp similar to clamp 24 is described in U.S. patent application Ser. No. 16/120,480 which is incorporated herein by reference.

Figure 2:
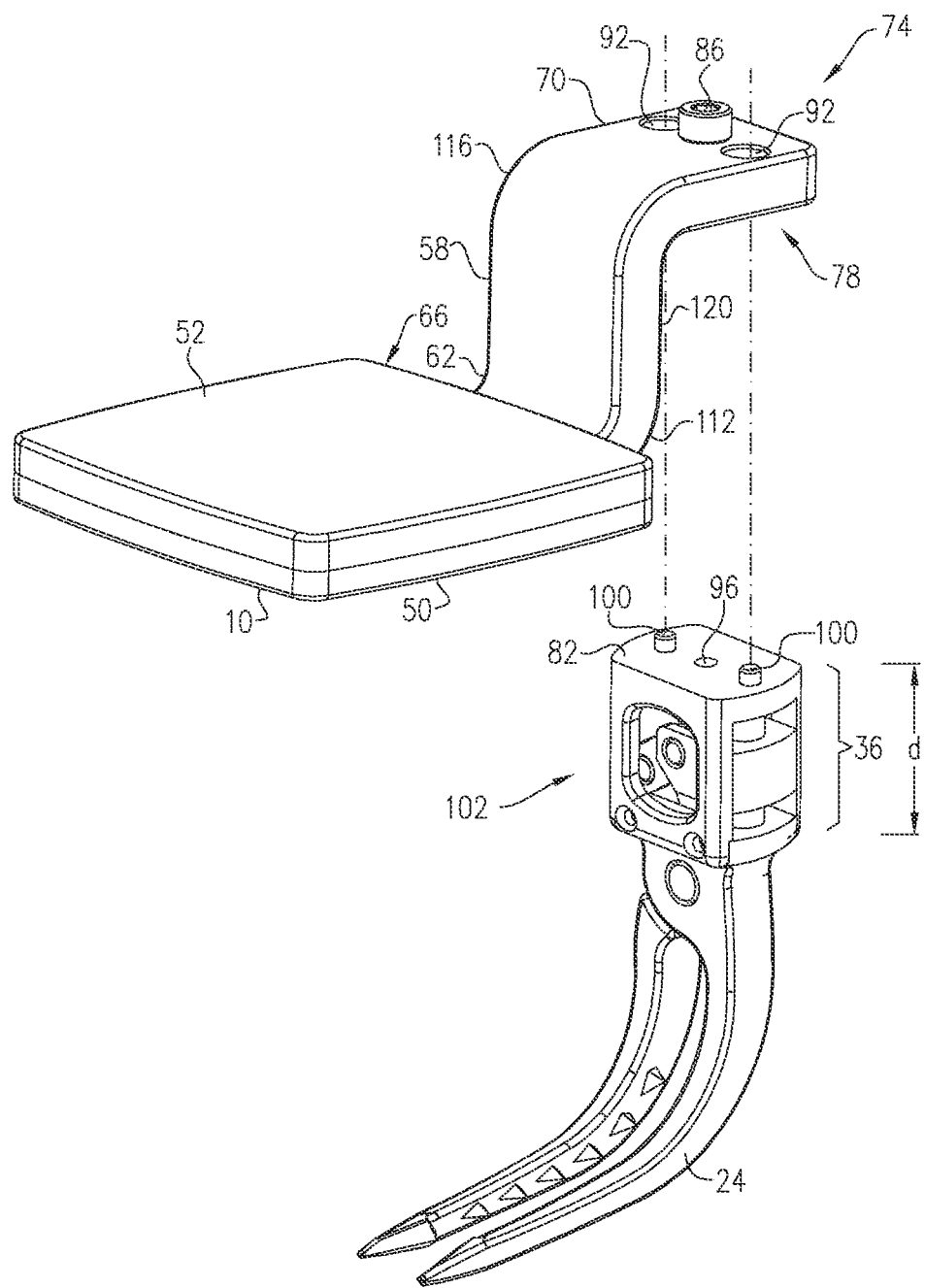
FIG. 2 is a schematic view of the device separated from a clamp, according to an embodiment of the present invention.
Figure 3:
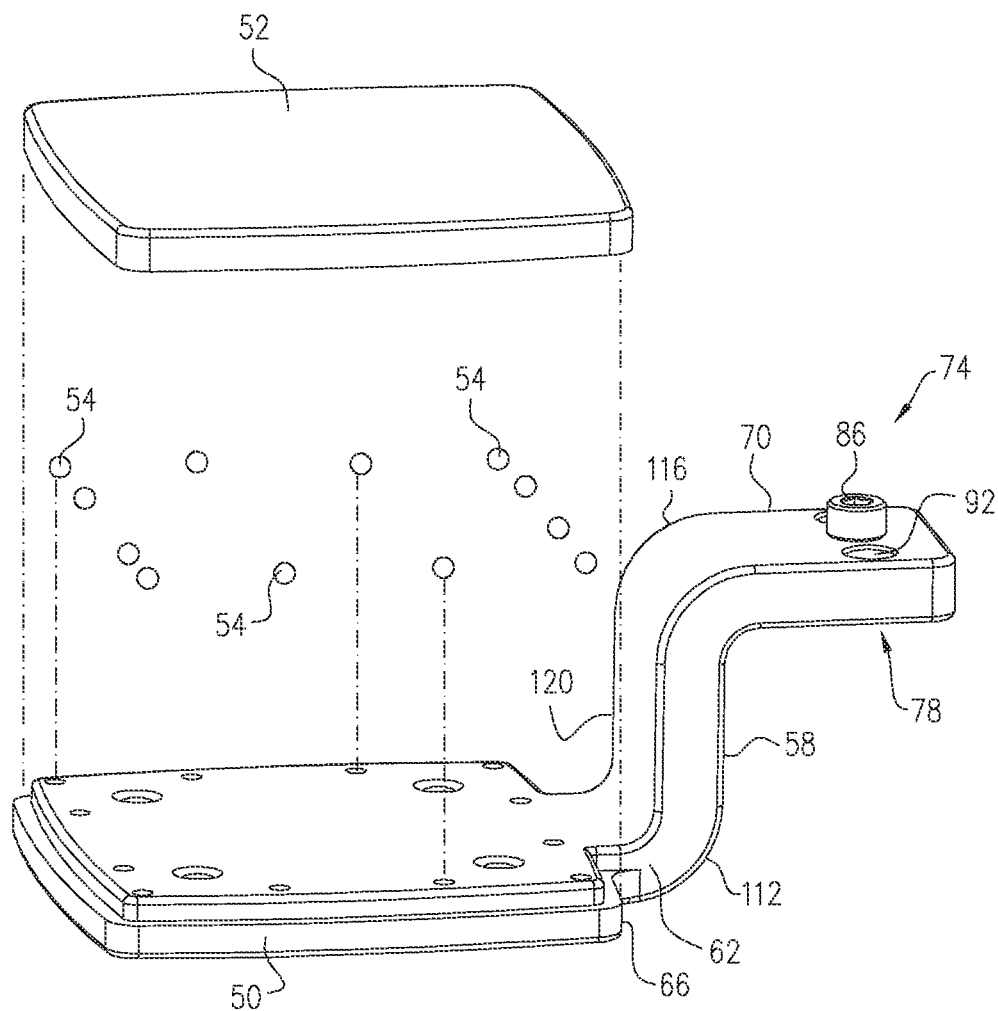
FIG. 3 is a schematic exploded view of the device, according to an embodiment of the present invention.

FIG. 2 is a schematic view of device 10 separated from clamp 24, and FIG. 3 is a schematic exploded view of device 10, according to an embodiment of the present invention. Device 10 comprises a radiotransparent plate 50, typically formed of a biocompatible plastic such as a polyimide. A plurality of substantially similar radiopaque elements 54, herein assumed to comprise spheres, are embedded within plate 50. Elements 54 are embedded within plate 50 in a predefined pattern, which is herein assumed to comprise points on sides of a rectangle. However, any other convenient predefined pattern may be used. In some embodiments the predefined pattern has no axis or plane of symmetry. Typically plate 50 is protected by a cover 52.

A radiotransparent sigmoid mounting arm 58, typically formed from the same biocompatible plastic as plate 50, is connected by a first end 62 of the arm to an edge 66 of the plate. A second end 70 of the arm contains one or more fastening receptacles 74 that enable the arm to be securely and fixedly fastened to support structure 36 in a predefined orientation. In embodiments of the invention, support structure 36 encloses adjustment elements 102 for clamp 24, the adjustment elements effectuating attachment of jaws of the clamp to a bone of patient 20. In an embodiment of the invention the support structure has differing depths d.

Second end 70 has a lower plane surface 78 which connects with an upper surface 82 of support structure 36. In a disclosed embodiment receptacles 74 comprise a captive screw 86 and holes 92, the screw and the holes mating respectively with a threaded hole 96 and studs 100 in upper surface 82.

As is apparent from the figures, the length of arm 58 determines the separation of plate 50 from lower surface 78 of the arm second end. Embodiments of the present invention comprise sets of devices 10, each member of the set being generally as described herein, but having a different known length of arm 58 from the other set members. Arm 58 is formed from two curved sections 112, 116, separated by a straight section 120, and the different lengths of the arm are formed by varying a length of straight section 120. In embodiments of the present invention the length of straight section 120 varies from 0 (zero) to up to approximately 7 cm, although values greater than 7 cm are possible. It will be understood that when the length of section 120 is 0 the two curved sections are connected together with no intervening straight section.

Each member of the set, comprising a respective plate 50 connected to a respective sigmoid mounting arm 58 in a step-like arrangement, may be formed as a single piece, typically by injection molding. It will be understood that each member of the set has known dimensions, so that there is a known mechanical offset between plate 50 and the second end of the arm, including the lower surface 78 of the arm second end.

Typically, for each member of a set of devices 10, the predefined pattern of radiopaque elements 54 is configured to have a one-to-one correspondence with the known mechanical offset. In this case, identification of the pattern provides a unique and unambiguous value for the mechanical offset, and providing the correspondence enables embodiments of the invention to support substantially any offset. As is described below, the correspondence may be stored in a computer memory, and the memory may be accessed so that the unique value of the mechanical offset for a given set member may be determined from the element pattern of the member.

In a disclosed embodiment plate 50 and lower surface 78 of device 10 are substantially parallel, and straight section 120 is perpendicular to the plate and to the lower surface. As stated above, the length of straight section 120 may be varied so as to provide sets of devices 10. Typically, a member of the set is selected so that cover 52 is below surface 82 of support structure 36, and so that plate 50 is as close to the skin of patient 20 as possible.

As stated above radiopaque elements are embedded within plate 50 in a predefined pattern, and the pattern may be in a one-one correspondence with the different mechanical offsets provided by the different lengths of straight section 120. For example, if the pattern is a rectangle, then the sides of the rectangle may be configured so that a different ratio of the lengths of the sides corresponds to a respective straight section length. Alternatively, the number of elements in a rectangle side may be varied, and the number configured to correspond to a length of section 120. As another example the shape of the pattern may be varied, and a different shape may be configured to correspond to a respective straight section length. Shapes may comprise a triangle, a quadrilateral, a pentagon, etc., but any convenient shape may be used.

In addition to the sets of devices 10 described above, embodiments of the present invention also comprise sets of clamps 24 with differing depths d of support structure 36. It will be understood that for any given arm length 58, the depth d of support structure 36 determines the separation of plate 50 from a given clamp selected from the sets of clamps 24.

Returning to FIG. 1, device 10 is typically selected from the set of devices 10, and clamp 24 is typically selected from the set of clamps 24 so that when the device is attached to upper surface 82 of support structure 36, plate 50 of the device is as close as possible to site 32, i.e., to the site of the operation to be performed in the procedure subsequent stage. Once a selected device 10 has been attached to surface 82, a computerized tomography (CT) scan of the device and of the patient's spine is performed. The scan may be performed by inserting patient 20 into a CT scanning facility, typically an intra-operative CT scanner. The insertion may be implemented by bringing the CT scanning facility to patient 20, or by transporting the patient to the facility.

A processing system 104, comprising a computer processor 108 coupled to a memory 114, receives the scan of device 10 and the patient's spine, and stores the scan as an image 118 in the memory. The one-to-one correspondence referred to above may also be stored in memory 114 as a correspondence 122. The processing system is configured to analyze the stored image so as to identify the pattern formed by radiopaque elements 54, and from the identified pattern to register a frame of reference of device 10, and thus of attached clamp 24, with a frame of reference of the patient's anatomy.

Figure 4:
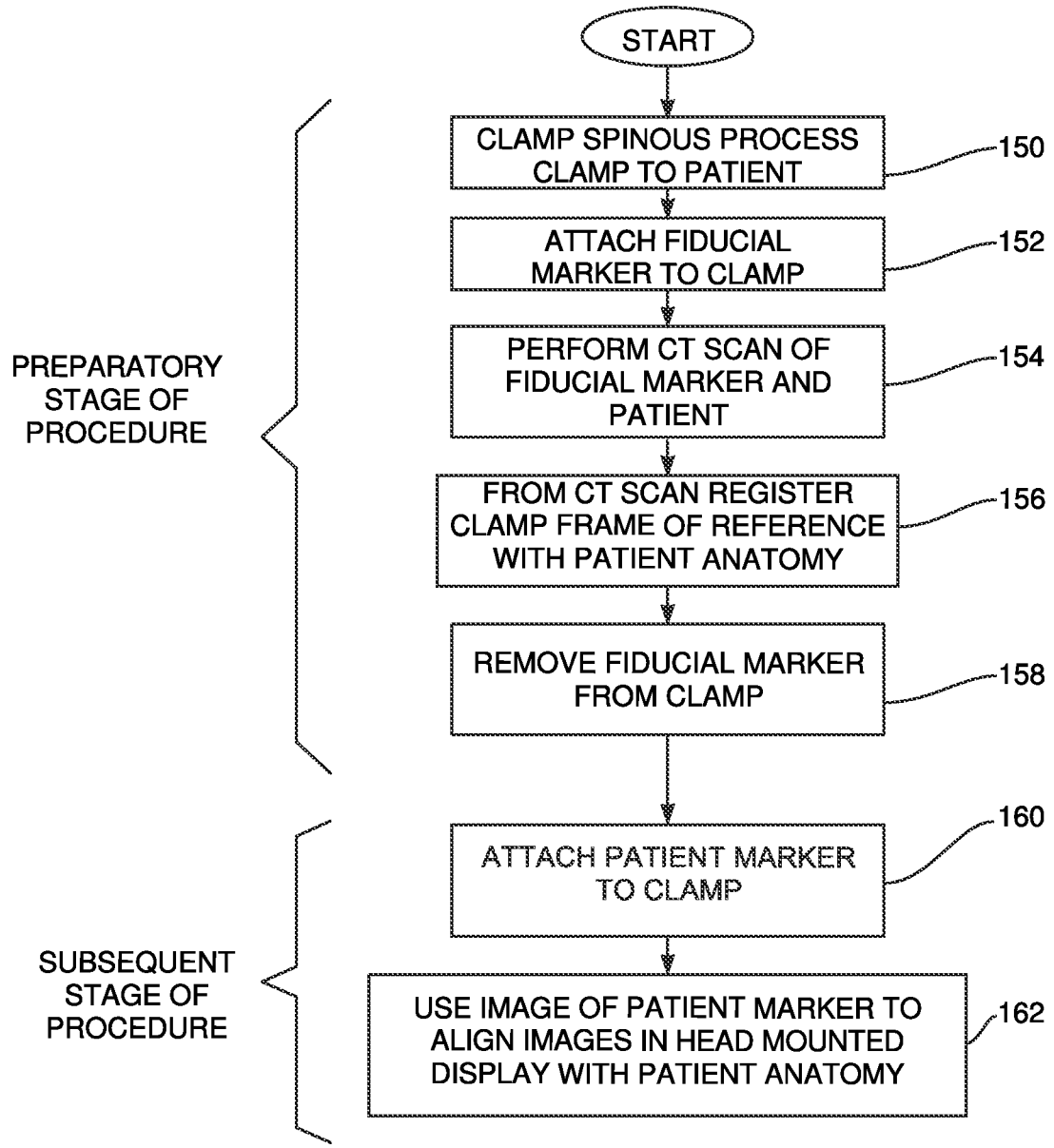
FIG. 4 is a flowchart of steps performed in both a preparatory stage and a subsequent stage of a procedure, according to an embodiment of the present invention.

FIG. 4 is a flowchart of steps performed in both the preparatory stage and the subsequent stage of the procedure, according to an embodiment of the present invention. In an initial step 150 and in an attachment step 152 of the preparatory stage, clamp 24 is inserted into patient 20 and clamped, using adjustment elements 102, to one or more spinous processes of the patient, and fiducial marker 10 is attached to support structure 36 of the clamp, as is described above with reference to FIG. 1. Steps 150 and 152 are performed by a user of the invention, typically professional 180 (referred to below).

In a scan step 154 a CT scan of marker 10, attached as described above, is performed, and image 118 of the scan is stored in memory 114. The CT scan may be accessed and stored by the processor of processing system 104. In an analysis step 156 the processing system analyzes the stored image, and from the analysis registers a frame of reference of marker 10, and thus of attached clamp 24, with a frame of reference of the patient's anatomy.

It will be appreciated that the registration of step 156 uses the known mechanical offset of plate 50 with lower surface 78 to provide a location and orientation of upper surface 82 of the clamp with respect to the frame of reference of the patient's anatomy. In the cases where the one-to-one correspondence referred to above is stored as correspondence 122 in memory 114, the processing system may determine the mechanical offset, in analysis step 156, from the pattern identified by the analysis, using the stored correspondence.

Analysis step 156 also determines a spatial transformation between the patient and the surgical clamp, and this is used, together with the mechanical offset, to calculate the registration between the two frames of reference.

In a concluding step 158 of the preparatory stage, fiducial marker 10 is removed from clamp 24, leaving upper surface 82 exposed. The user of the invention performs concluding step 158.

Figure 5:
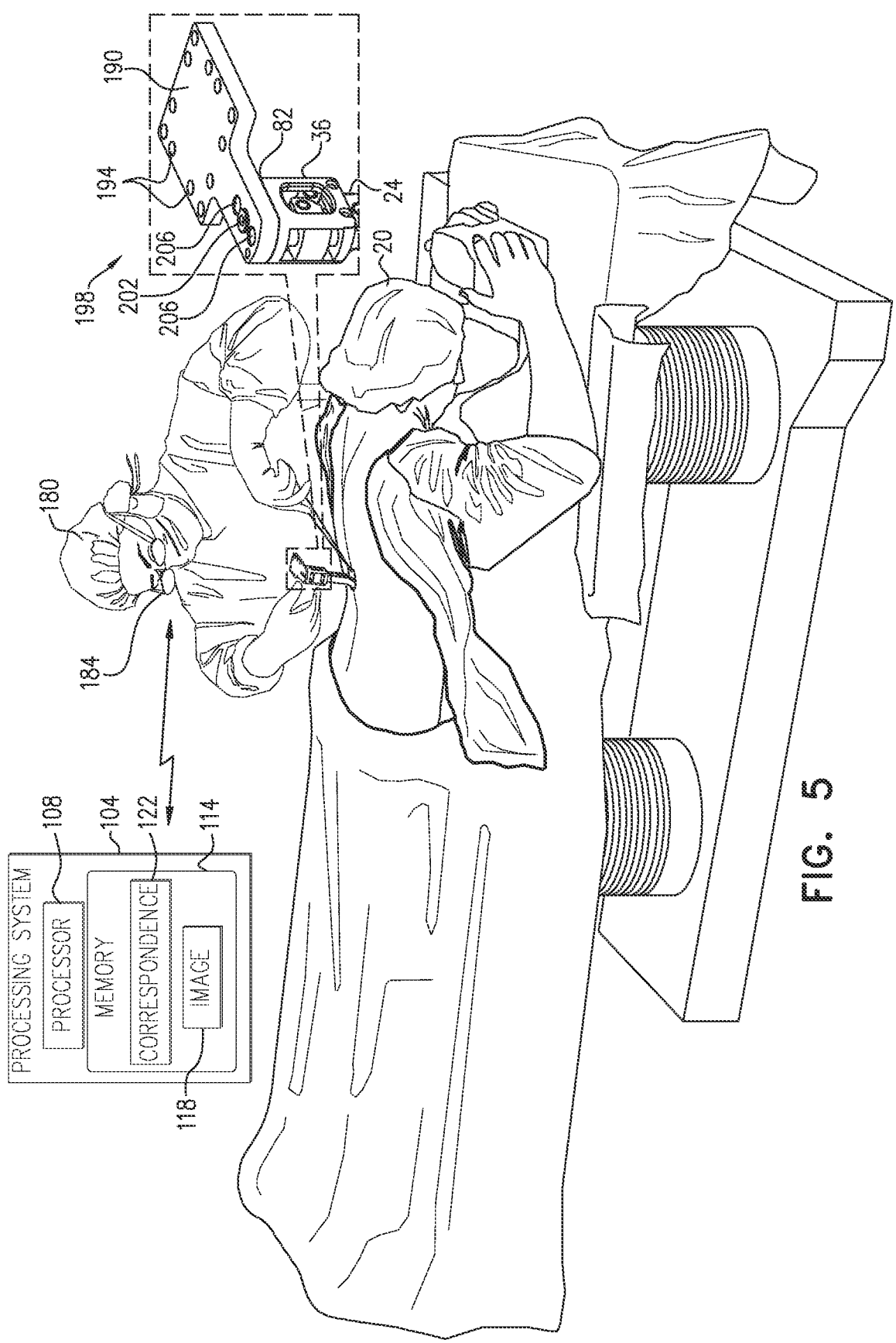
FIG. 5 is a schematic illustration of the subsequent stage of the procedure, according to an embodiment of the present invention.

FIG. 5 is a schematic illustration of the subsequent stage of the procedure, according to an embodiment of the present invention. In the subsequent stage a patient marker attachment step 160 and an alignment step 162 are performed, and these steps are described further below. In the subsequent stage, a medical professional 180 operates on the patient. Professional 180 wears an augmented reality head-mounted display (HMD) 184, which is configured to present stored images that are aligned with the patient, to the professional. In order to operate, HMD 184 is coupled to processor 108 of system 104 and the stored images may be stored in memory 114. Alternatively, HMD 184 has its own dedicated processor which performs similar functions to those performed by processor 108. A head-mounted display similar to HMD 184 is described in U.S. Pat. No. 9,928,629, which is incorporated herein by reference.

To perform the alignment for HMD 184, in attachment step 160 a patient marker 190 with known, preset, dimensions, is attached to upper surface 82 of support structure 36 of clamp 24. Patient marker 190 may be attached in a selected pre-determined orientation. Marker 190 comprises fastening receptacles 198, substantially similar to receptacles 74, so that in the disclosed embodiment referred to above receptacles 198 comprise a captive screw 202 and holes 206, the screw and the holes mating respectively with threaded hole 96 and studs 100 in upper surface 82 of clamp 24. A patient marker similar to marker 190 is described in PCT Patent Application PCT/IB2019/053524, which is incorporated herein by reference. Attachment step 160 is performed by professional 180. As is described in PCT Patent Application PCT/IB2019/053524, a patient marker such as marker 190 may be configured to be attached in a number of discrete pre-determined orientations to upper surface 82. Thus, all such pre-determined orientations for patient marker 190 are assumed to be comprised within the scope of the present invention.

Marker 190 comprises optical reflectors 194 incorporated into the surface of the patient marker, and the reflectors are arranged in a predetermined pattern so that an image of the reflectors can be analyzed so as to provide an unambiguous measure of the location and of the orientation of the marker.

In alignment step 162 the HMD projects visible or invisible light to patient marker 190, and acquires images of reflectors 194 of the marker. From the acquired images, the HMD processor determines the location and orientation of the patient marker. Since the patient marker has known dimensions, and is attached to upper surface 82, the processor applies the registration found in step 156 (between the frames of reference of fiducial marker 10 and the patient's anatomy) to ensure that the images projected by the HMD align with the anatomy of patient 20. Alignment step 162 is performed by processing system 104.

As is stated above, a user performs steps 150, 152, 158, and 160, and processor 108 of processing system 104 performs the access and storage portions of step 154, as well as steps 156, and 162. Thus, in the user steps described above, professional 180 inserts clamp 24 into patient 20, and attaches the clamp to the spinous processes of the patient. The professional then attaches fiducial marker 10 to the clamp. In some embodiments, the professional selects the fiducial marker from a set of different fiducial markers so that plate 50 is as close to the skin of patient 20 as possible. Thus, the professional chooses the fiducial marker with a length of arm 58, that achieves this goal. In some embodiments the clamp has different lengths, and there may be a spacer (described in more detail below) connecting the marker to the clamp. In this case the operator may select one or a combination of the clamp, the spacer (if used) and/or the fiducial marker to achieve the goal. At the conclusion of the preparatory stage of the procedure, and at the beginning of the subsequent stage, the professional detaches the fiducial marker and any spacer that has been used, and attaches patient marker 190 to clamp 24.

In performing the portions of step 154, and steps 156, and 162, processor 108 accesses and stores an acquired CT scan of the attached fiducial marker, and stores an image of the scan in memory 114. The processor then analyzes the image so as to register a frame of reference of the fiducial marker with a frame of reference of the patient's anatomy. Once the fiducial marker has been detached from the clamp, and the patient marker has been attached, the processor acquires or accesses an image of the attached patient marker, and analyzes the image to determine the location and orientation of the patient marker with respect to the operator. Using the known spatial dimensions of the patient marker and its attachment in a known, determined, orientation to the clamp, the processor uses the registration referred to above, and the acquired image of the patient marker, to ensure that the projected HMD images align with the anatomy of patient 20 as seen from the point of view of the user.

In an alternative embodiment, rather than calculating the registration between the frames of reference of the patient and the fiducial marker, as is described above for scan step 154 and analysis step 156, in step 156 the processing system uses the scan of step 154, wherein the CT scan scans the fiducial marker and the patient's anatomy, to find physical dimensions relating upper surface 82 of the clamp to the attached spinous processes of the patient.

In the alternative embodiment, in alignment step 162, the HMD processor uses the images of reflectors 194 to unambiguously determine the location and orientation of patient marker 190, which is attached to upper surface 82 of the clamp. Alternatively, the location and orientation of the patient marker may be determined unambiguously by any convenient method known in the art.

In the alternative embodiment HMD processor uses the known dimensions of the patient marker, and its unambiguously determined location and orientation with respect to the clamp, together with the physical dimensions relating the clamp to the patient's spinous processes, to calculate a spatial relationship between the patient marker and the spinous processes. It will be understood that the spatial relationship enables the HMD processor to form a direct registration between the frames of reference of the patient marker and the spinous processes, i.e., the patient's anatomy, so that the processor does not need to calculate the registrations between the frames of reference of the patient marker and the clamp, and between the frames of reference of the clamp and the patient's anatomy.

The description above provides details of how fiducial marker 10 and patient marker 190 may be attached, via clamp 24, as close as possible to site 32, i.e., to the site of the operation performed on patient 20. The following description provides further details of embodiments of the invention which may be used, alternatively or additionally, so that the patient marker and the fiducial marker are as close as possible to the site of the operation.

Figure 6:
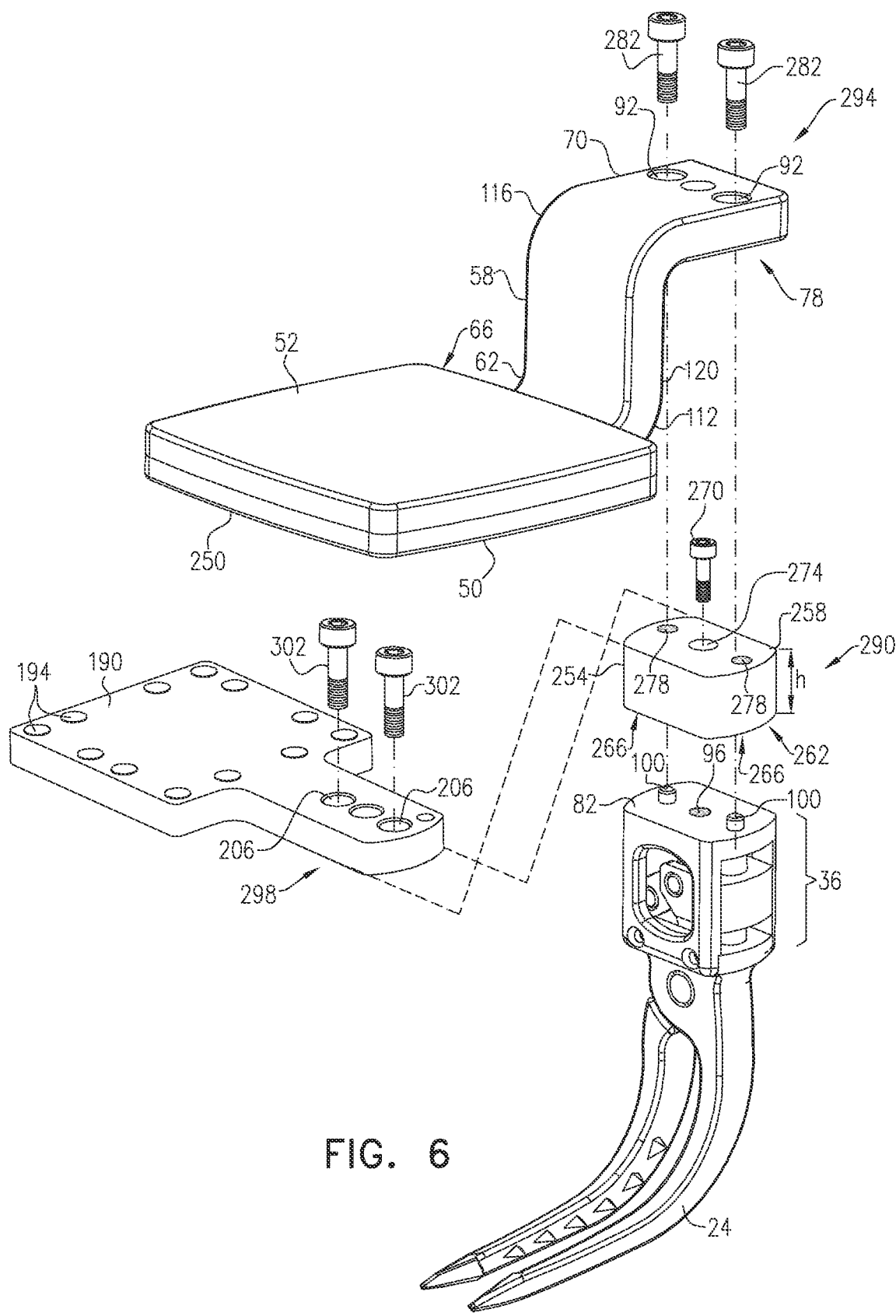
FIGS. 6, 7, and 8 are schematic views of a medical marking device, according to alternative embodiments of the present invention.

FIG. 6 is a schematic view of a medical marking device 250 separated from clamp 24, according to an alternative embodiment of the present invention. Apart from the differences described below, the operation of device 250 is generally similar to that of device 10 (FIGS. 1-5), and elements indicated by the same reference numerals in both devices 250 and 10 are generally similar in construction and in operation. Device 250 is herein also termed fiducial marker 250.

In contrast to device 10, wherein second end 70 of the sigmoid arm is configured to connect directly to upper surface 82 of support structure 36, in device 250 there is an intervening spacer 254 between the sigmoid arm second end and surface 82. Spacer 254 is formed to have a pair of opposing parallel surfaces, an upper spacer surface 258 and a lower spacer surface 262, separated by a preset fixed distance h. When assembled, lower surface 262 fixedly mates with upper surface 82 of support structure 36, and lower surface 78 of the sigmoid arm removably mates with upper surface 258 of spacer 254.

So that lower spacer surface 262 can fixedly mate with support structure surface 82, the lower spacer surface has two blind holes 266 inlet into the lower spacer surface that align with and fit to studs 100. In addition, spacer 254 comprises a captive screw 270, residing in a hole 274 of the spacer. The captive screw is configured so that when it is screwed into threaded hole 96 it fastens the spacer fixedly to support structure 36, while the head of screw 270 is within hole 274 and below upper surface 258 of the spacer. Captive screw 270 and blind holes 266 act as spacer lower surface fastening receptacles 290.

Once spacer 254 is fixed to support structure 36, sigmoid arm lower surface 78 may be removably mated with the upper surface of the spacer. The spacer upper surface comprises two threaded holes 278 which align with holes 92. To removably mate the sigmoid arm lower surface with the spacer, a pair of retaining screws 282 pass through holes 92, and are screwed into threaded holes 278. Screws 282 and threaded holes 278 act as spacer upper surface fastening receptacles 294.

Spacer 254 is typically part of a set of such spacers. In one embodiment spacers of the set have values of h in a range of 1 cm-5 cm, but in other embodiments the set has different ranges of h. Spacer 254 is used to raise plate 50 above clamp 24 while keeping the plate as close as possible to the patient's spine, and the value of h of a selected spacer may be chosen according to patient characteristics. It will be understood that having a set of spacers 254 with different values of h replaces, or is in addition to, the requirement of different lengths of arm 58 referred to above for a set of devices 10.

During a procedure where marker 250 is used, after it has been attached, as described above, to the upper surface of spacer 254, it may be scanned fluoroscopically, and may then be removed from the spacer upper surface. After removal, as illustrated in FIG. 6, patient marker 190 may then be attached to the spacer upper surface. The patient marker attachment is implemented by screws 302, substantially similar to screws 282, penetrating holes 206 and being screwed into threaded holes 278. Screws 302 and threaded holes 278 act as fastening receptacles 298 for the patient marker, receptacles 298 being substantially similar to receptacles 294.

Referring back to the flowchart of FIG. 4, when marker 250 is used in place of marker 10, the actions described above for each of the steps of the flowchart are substantially similar, except as follows.

In step 152, spacer 254 is first fixedly attached to support structure 36, and then fiducial marker 250 is removably attached to the spacer, as described above.

In step 158 fiducial marker 250 is removed from the spacer, and in step 160 patient marker 190 is attached to the spacer, as described above.

It will be understood that because fiducial marker 250 and patient marker 190 are attached to the same location, the upper surface of the spacer, the registration found in step 156 can be used in alignment step 162.

Figure 7:
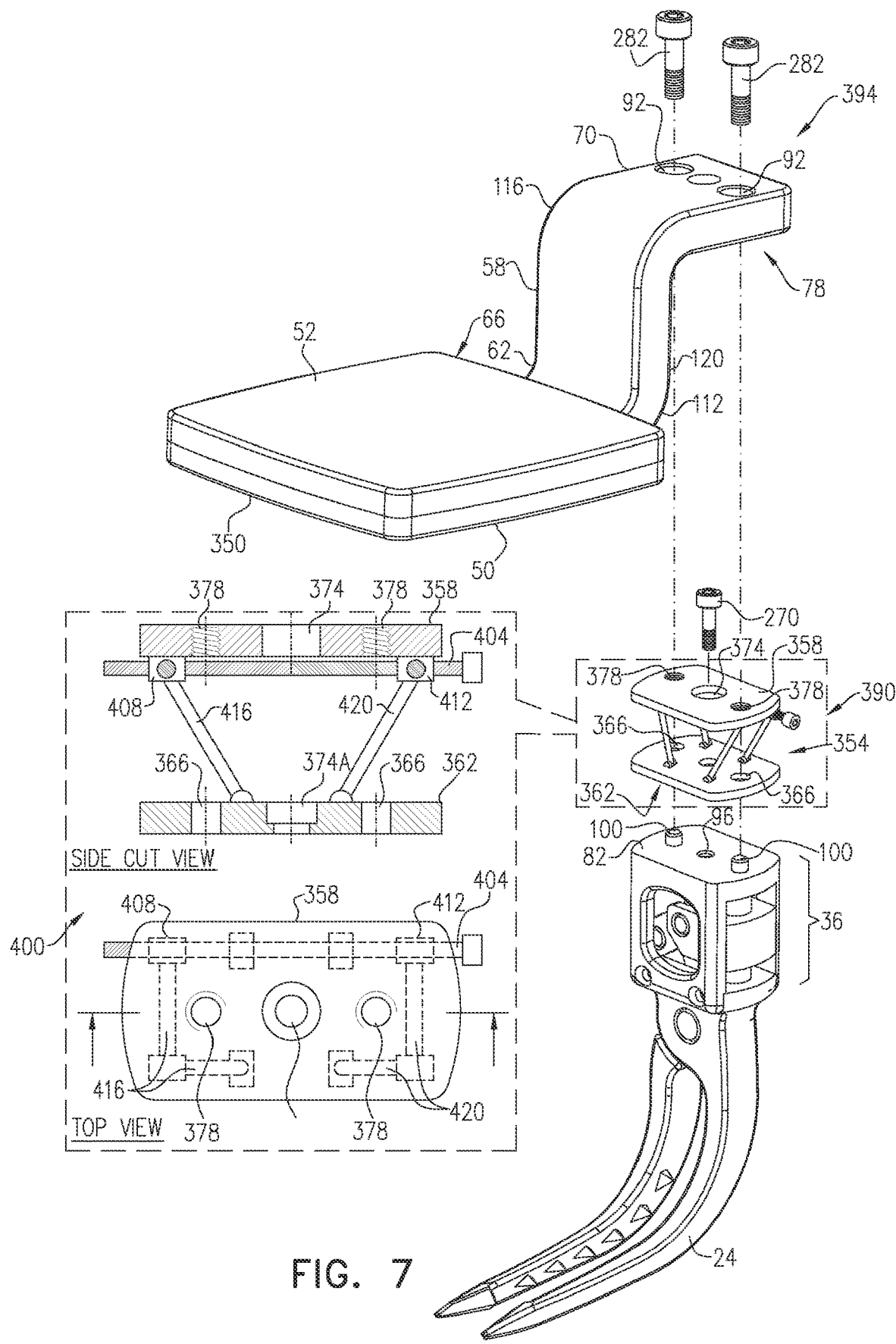

FIG. 7 is a schematic view of a medical marking device 350 separated from clamp 24, according to an alternative embodiment of the present invention. Apart from the differences described below, the operation of device 350 is generally similar to that of device 250 (FIGS. 1-6), and elements indicated by the same reference numerals in both devices 250 and 350 are generally similar in construction and in operation. Device 350 is herein also termed fiducial marker 350.

In contrast to device 250, which uses spacer 254 with a preset fixed distance between the upper and lower surfaces of the spacer, device 350 uses a spacer 354, herein also termed adjustable spacer 354, which has adjustable distances between an upper adjustable spacer plate 358 and a lower adjustable spacer plate 362. Elements in the two plates of adjustable spacer 354 correspond to respective elements in the two surfaces of fixed spacer 254. Thus, in upper plate 358 threaded holes 378 and a hole 374 are substantially similar to holes 278 and 274, so that hole 374 permits passage of captive screw 270. Screws 282 and threaded holes 378 act as upper adjustable spacer plate fastening receptacles 394.

In lower plate 362 holes 366 are substantially similar in diameter and position to blind holes 266, although holes 366 are not necessarily blind. Lower plate 362 also comprises a hole 374A, which aligns with hole 374 and which is sized to retain screw 270. Captive screw 270 and holes 366 act as lower adjustable spacer plate fastening receptacles 390.

Adjustable spacer 354 comprises an adjustable mechanism 400, which connects the lower and upper plates of adjustable spacer 354. Mechanism 400 maintains the upper plates substantially parallel to each other, while operation of the mechanism adjusts the separation of the plates.

In one embodiment, illustrated in FIG. 7, mechanism 400 comprises a rod 404 having clockwise and counterclockwise threads, and the threads are configured to mate with respective nuts 308, 412 slidingly attached to upper plate 358. Mechanism 400 further comprises two levers 416, 420, having their fulcra coupled to lower plate 362, and their endpoints attached to the respective nuts. Rotation of rod 404 of mechanism 400 increases or decrease the nut separation, and correspondingly decreases or increases the separation between the upper and lower plates of adjustable spacer 354.

Other mechanisms for connecting the upper and lower plates of spacer 354, that maintain the plates substantially parallel to each other while providing adjustable separation of the plates, will be apparent to those having ordinary skill in the art. All such mechanisms are assumed to be comprised within the scope of the present invention.

Referring back to the flowchart of FIG. 4, when marker 350 is used in place of marker 10, the actions described above for each of the steps of the flowchart are substantially similar, except as follows.

In step 152, lower plate 362 is first fixedly attached to support structure 36, and then fiducial marker 350 is removably attached to upper plate 358, as described above.

In step 158 fiducial marker 350 is removed from the spacer upper plate 358, and in step 160 patient marker 190 is attached to the spacer upper plate, as described above.

It will be understood that because fiducial marker 350 and patient marker 190 are attached to the same location, the upper surface of the spacer upper plate, the registration found in step 156 can be used in alignment step 162.

Figure 8:
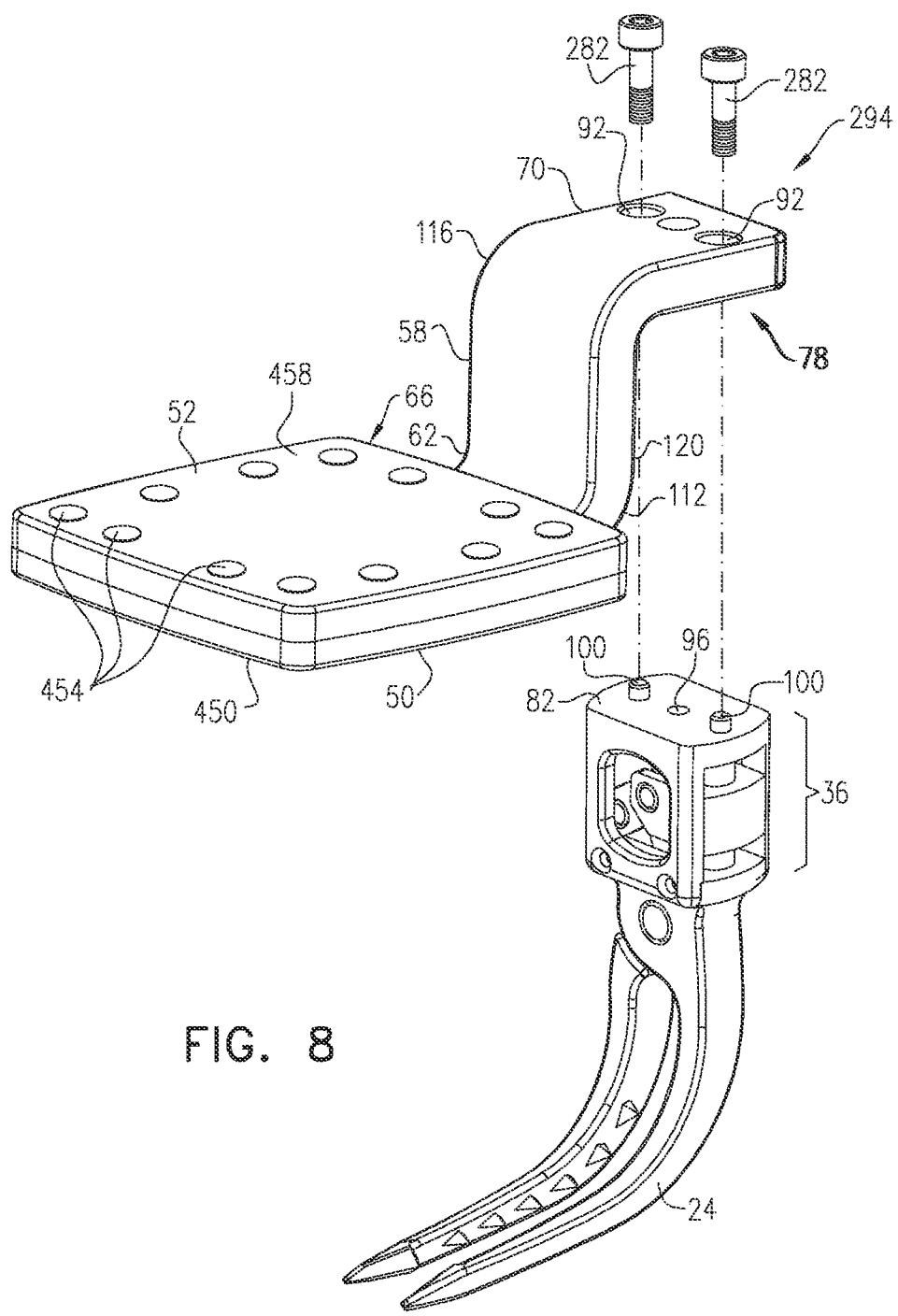

FIG. 8 is a schematic view of a medical marking device 450 separated from clamp 24, according to an alternative embodiment of the present invention. Apart from the differences described below, the operation of device 450 is generally similar to that of device 250 (FIGS. 1-6), and elements indicated by the same reference numerals in both devices 250 and 450 are generally similar in construction and in operation. Device 450 is herein also termed fiducial marker 450.

In contrast to device 250, a plurality of optical reflectors 454 are positioned on a surface 458 of cover 52 of plate 50. In one embodiment reflectors 454 are arranged on the surface in a predetermined pattern, typically with no rotational axis of symmetry (other than a trivial axis of symmetry for rotating by 360° and no mirror plane of symmetry. The predetermined pattern is configured so that an image of the reflectors can be analyzed so as to provide an unambiguous measure of the location and of the orientation of plate 50. The imaging of reflectors 454, and the analysis of the image, is substantially as described above for reflectors 194 of patient marker 190.

Device 450 is typically used with spacer 254 and/or spacer 354, described above with reference to FIGS. 6 and 7. When used device 450 is used with one of these spacers, patient marker 190 may be positioned with respect to the spacer as described above. However, because of the presence of reflectors 454, patient marker 190 may instead be positioned in any other convenient location, as is explained below with reference to changes in the flowchart of FIG. 4.

For clarity, in the following description of changes to the flowchart, device 450 is assumed to be used with spacer 254. Those having ordinary skill in the art will be able to adapt the description, *mutatis mutandis*, if device 450 is used with spacer 354 or with any other spacer effectively separating plate 50 from support structure 36.

In step 152 of the flowchart, spacer 254 is first attached to support structure 36 using screw 270, and then fiducial marker 450 is attached to the spacer using screws 282, as described above.

Steps 154 and 156 are performed as described above with reference to FIG. 4, so as to register a frame of reference of marker 450, and thus of attached clamp 24, with a frame of reference of the patient's anatomy.

In step 158, prior to removal of fiducial marker 450 from the spacer, reflectors 454 of the marker are optically scanned and are imaged using HMD 184. The processor associated with HMD 184 analyzes the image to find the location and orientation of the reflectors, and thus of plate 50, in the frame of reference of the HMD. Marker 450 may then be removed from spacer 254, and the spacer may be removed from support structure 36.

Steps 160 and 162 are implemented generally as described above, so that in step 160 patient marker 190 is attached to upper surface 82 of support structure 36.

In step 162 patient marker 190 is optically scanned and is tracked, and the processor of the HMD is able to use the location and orientation of plate 50 found in step 158 to generate a correction vector, between the positions of the plate and the positions of the patient marker. The correction vector corrects for the fact that the fiducial marker and the patient marker are attached to different locations (i.e., the spacer and the support structure). In step 162 the HMD processor applies this correction vector to ensure that the images projected by the HMD align with the anatomy of patient 20.

The description above is for a particular case where patient marker 190 and fiducial marker 450 are attached to different elements related to clamp 24. Those having ordinary skill in the art will be able to adapt the description, mutatis mutandis, for other cases of different attachments, and all such cases are assumed to be comprised with the scope of the present invention.

The scans in steps 158 and 162 are separate scans, so that typically the HMD is in different locations for the scans. In step 158, because of the known dimensions of fiducial marker 450 and spacer 254, the processor associated with the HMD is able to find a local fiducial marker vector relating the location of plate 50 to lower surface 78, and thus to upper surface 82 of support structure 36. It will be appreciated that this method of finding a local fiducial marker applies to all fiducial markers, with or without a spacer, of the present invention, In scan 162, patient marker 190 is scanned. The dimensions of the patient marker are known, and reflectors 194 of the patient marker are arranged so that, as stated above, an image of the reflectors is able to provide an unambiguous spatial relation between the operator and the patient marker. The HMD processor analyzes the scanned image of the patient marker (to determine the spatial relation between the operator and the patient marker), and from its determined location and orientation with respect to the patient (or support structure 36) finds a local patient marker vector relating the location of the patient marker to support structure 36, e.g., upper surface 82.

It will be understood that the correction vector between the positions of plate 50 and of patient marker 190 may correspond to the sum of the local fiducial marker vector and the local patient marker vector.

By using the image of the patient marker reflectors to find the location and orientation of the patient marker, it will be understood that even in the case of different possible orientations of the patient marker, other than that illustrated in the figures, the HMD processor is able to find the correction vector. Alternatively or additionally, the processor may be configured to use any other method known in the art for finding the orientation of the patient marker. For example, PCT Patent Application PCT/IB2019/053524, referred to above, describes how the orientation of a patient marker may be determined, The description above has assumed that during a procedure, device 450 is removed, and is replaced by patient marker 190. However, because of reflectors 454, it will be appreciated that imaging of the reflectors enables device 450 itself to be used as a patient marker. Consequently, in some embodiments of the present invention, device 450 is not removed, and acts both as a fiducial marker and as a patient marker.

Returning to the flowchart of FIG. 4, and applying it also to the embodiments described above with reference to FIGS. 6, 7, and 8, a user performs steps 150, 152, 158, and 160, and processor 108 of processing system 104 performs the portions of step 154, and steps 156 and 162. Thus, in the user steps described above, professional 180 inserts clamp 24 into patient 20, and attaches the clamp to the spinous processes of the patient. The professional then attaches fiducial marker 10, 250, 350, or 450 to the clamp. In the cases of markers 250, 350, and 450 the markers are attached using spacer 254 and/or adjustable spacer 354. In selecting which marker to be used, and, where appropriate, which spacer is used, the professional chooses the length of the arm of the marker and the size of the spacer so that plate 50 is as close to the skin of patient 20 as possible. Thus, the professional chooses the fiducial marker with a length of arm 58, and, when spacer 254 is used, the spacer having a value of distance h, that achieves this goal. At the conclusion of the preparatory stage of the procedure, and at the beginning of the subsequent stage, the professional detaches the fiducial marker and any spacer that has been used, and attaches patient marker 190 to clamp 24.

Thus, for the embodiment described above with reference to FIG. 8, as well as the for the other embodiments described herein, in performing the portion of step 154, and steps 156 and 162, processor 108 accesses a CT scan of the attached fiducial marker, and stores an image of the scan in memory 114. The processor then analyzes the image so as to register a frame of reference of the fiducial marker with a frame of reference of the patient's anatomy. Once the fiducial marker has been detached from the clamp, and a patient marker having a known orientation when connected to the clamp, has been attached, the processor accesses or acquires an image of the attached patient marker, and analyzes the image to determine the location and orientation of the operator with respect to the patient marker. Using the known spatial dimensions of the patient marker and its known orientation when connected to the clamp, the processor uses the registration referred to above, and the acquired image of the patient marker, to ensure that the projected HMD images align with the anatomy of patient 20 as seen from the point of view of the user. In addition, as is described above, processor 108 may also use the patient marker image to form a registration between a patient marker frame of reference and a frame of reference of the patient's anatomy.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising:
   rigidly attaching a retaining structure to a bone of a patient;
   connecting a first end of a sigmoid mounting arm to the retaining structure, the sigmoid mounting arm having a second end fixedly connected to a plate that has a first plurality of optical reflectors positioned in a first predefined pattern on a surface thereof;
   optically scanning the first plurality of optical reflectors so as to form a first optical scan;
   disconnecting the first end of the sigmoid mounting arm from the retaining structure and connecting a patient marker, having a second plurality of optical reflectors in a second predefined pattern, to the retaining structure;
   optically scanning the second plurality of optical reflectors so as to form a second optical scan; and
   causing one or more computer processors to:
   derive from the first and the second optical scans a correction vector indicative of a difference between a location and an orientation of the plate and a location and an orientation of the patient marker; and
   in response to the correction vector, register a frame of reference of the patient with a frame of reference of the patient marker.

2. The method according to claim 1 and comprising:
   mounting a head-mounted display, having a camera configured to acquire the first and second optical scans, on a head of an operator of an augmented reality system;

acquiring the first optical scan with the camera while the operator and the camera are in respective first locations; and acquiring the second optical scan with the camera while the operator and the camera are in respective second locations, different from the respective first locations.

3. The method according to claim 2, further comprising causing the one or more computer processors to:

determine a local fiducial marker vector relating a location of the plate to a region of the retaining structure from the first optical scan, and determine a local patient marker vector relating a location of the patient marker to the region of the retaining structure.

4. The method according to claim 3, further comprising forming the correction vector as a sum of the local fiducial marker vector and the local patient marker vector.

5. The method according to claim 3, wherein the region of the retaining structure comprises a surface of the retaining structure, and wherein connecting the first end of the sigmoid mounting arm to the retaining structure comprises mounting the first end on the surface, and wherein connecting the patient marker to the retaining structure comprises connecting the patient marker to the surface.

6. The method according to claim 1, wherein connecting the patient marker to the retaining structure comprises attaching the patient marker to the retaining structure in a selected one of a plurality of different discrete orientations.

7. The method according to claim 1, wherein the retaining structure comprises at least one of a pin rigidly inserted into the bone of the patient or a clamp rigidly attached to the bone of the patient.

8. A computer-implemented method for performing an augmented reality procedure on a patient, wherein an operator of the procedure wears a head-mounted display and rigidly attaches a retaining structure to a bone of the patient, attaches a fiducial marker to the retaining structure, then detaches the fiducial marker from the retaining structure and attaches a patient marker to the retaining structure, the method comprising;

accessing a computerized tomography scan of the attached fiducial marker;

storing an image of the computerized tomography scan in a memory;

analyzing the stored image so as to determine a registration of a frame of reference of the fiducial marker with a frame of reference of an anatomy of the patient;

acquiring an image of the patient marker while the patient marker is attached to the retaining structure that is rigidly attached to the bone of the patient; and using the registration and the acquired image to align images projected on the head-mounted display with the anatomy of the patient as seen from a point of view of the operator of the procedure.

9. The method according to claim 8, wherein using the acquired image comprises analyzing the acquired image to determine a location and an orientation of the operator with respect to the patient marker.

10. The method according to claim 8 and comprising using the acquired image to form a registration between a patient marker frame of reference and a frame of reference of the anatomy of the patient.

11. The method according to claim 8, wherein attaching the patient marker to the retaining structure comprises attaching the patient marker to the retaining structure in a selected one of a plurality of different discrete orientations.

12. The method according to claim 8, wherein the fiducial marker is attached to the retaining structure by a sigmoid mounting arm.

13. The method according to claim 8, wherein the fiducial marker comprises a plurality of optical reflectors in a first predefined pattern, and the method further comprises optically scanning the plurality of optical reflectors while the patient marker is attached to the retaining structure that is rigidly attached to the bone of the patient.

14. The method according to claim 8, wherein the retaining structure comprises at least one of a pin rigidly inserted into the bone of the patient or a clamp rigidly attached to the bone of the patient.

* * * * *